(12) United States Patent
Morré et al.

(10) Patent No.: US 7,053,188 B2
(45) Date of Patent: May 30, 2006

(54) MONOCLONAL ANTIBODIES SPECIFIC FOR NEOPLASIA-SPECIFIC NADH:DISULFIDE REDUCTASE

(75) Inventors: D. James Morré, West Lafayette, IN (US); NaMi McCarty, Cambridge, MA (US); Dorothy Morré, West Lafayette, IN (US); Pin-Ju Chueh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 70 days.

(21) Appl. No.: 10/373,579

(22) Filed: Feb. 24, 2003

(65) Prior Publication Data

US 2003/0170757 A1 Sep. 11, 2003

Related U.S. Application Data

(60) Provisional application No. 60/359,070, filed on Feb. 22, 2002.

(51) Int. Cl.
*C07K 16/00* (2006.01)

(52) U.S. Cl. .............................. 530/388.1; 530/388.26; 530/388.8

(58) Field of Classification Search .............. 530/387.1, 530/388.1, 388.26, 388.8; 424/130.1, 141.1, 424/146.1, 155.1, 138.1; 435/7.1, 7.92, 69.6
See application file for complete search history.

(56) References Cited

U.S. PATENT DOCUMENTS

| | | | |
|---|---|---|---|
| 3,817,837 A | | 6/1974 | Rubenstein et al. |
| 3,850,752 A | | 11/1974 | Schuurs et al. |
| 3,939,350 A | | 2/1976 | Kronick et al. |
| 3,996,345 A | | 12/1976 | Ullman et al. |
| 4,263,279 A | | 4/1981 | Sela et al. |
| 4,275,149 A | | 6/1981 | Litman et al. |
| 4,277,437 A | | 7/1981 | Maggio |
| 4,331,647 A | | 5/1982 | Goldenberg |
| 4,348,376 A | | 9/1982 | Goldenberg |
| 4,361,544 A | | 11/1982 | Goldenberg |
| 4,366,241 A | | 12/1982 | Tom et al. |
| 4,460,561 A | | 7/1984 | Goldenberg |
| 4,624,846 A | | 11/1986 | Goldenberg |
| 4,952,394 A | | 8/1990 | Senter |
| 4,986,979 A | | 1/1991 | Morgan, Jr. et al. |
| 5,037,630 A | | 8/1991 | Fritzberg et al. |
| 5,089,249 A | | 2/1992 | Fritzberg et al. |
| 5,270,202 A | * | 12/1993 | Raychaudhuri |
| 5,332,567 A | | 7/1994 | Goldenberg |
| 5,541,297 A | | 7/1996 | Hansen et al. |
| 5,569,673 A | | 10/1996 | Morré et al. |
| 5,605,810 A | | 2/1997 | Morré et al. |
| 5,716,595 A | | 2/1998 | Goldenberg |
| 6,235,280 B1 | * | 5/2001 | Chatterjee et al. |
| 6,395,276 B1 | | 5/2002 | Rybak et al. |
| 6,632,431 B1 | * | 10/2003 | Wu |

FOREIGN PATENT DOCUMENTS

| | | |
|---|---|---|
| WO | 95/26743 | 12/1995 |
| WO | 01/032673 | 10/2001 |

OTHER PUBLICATIONS

Jain R. K. Scientific American, 271(1):58–65, Jul. 1994.*
Dillman R. O. Annals of Internal Medicine, 111:592–603, 1989.*
Weiner L. M. Seminars in Oncology, 26 (4 Suppl 12):41–50, Aug. 1999.*
Dillman, R. O. Journal of Clinical Oncology, 12(7):1497–1515, 1994.*
Freshney R. I. Culture of Animal Cells, A Manual of Basic Technique, Alan R. Liss, Inc., 1983, New York, p. 3–4.*
Dermer G. B. Bio/Technology, 12:320, Mar. 12, 1994.*
Jessani et al. Proc. Natl. Acad. Sci, USA, 101(38):13756–13761, Sep. 21, 2004.*
Cho et al. Proceedings of the American Association for Cancer Research 39: 347, 1998, abstract #2972.*
FUNDAMENTAL IMMUNOLOGY 242, William E. Paul, M.D. ed., 3d ed. 1993.*
Yantiri et al. Archives of Biochemistry and Biophysics 358(2): 336–342, 1998.*
Campbell A. M. Monoclonal Antibody Technology, Chapter 1:1–32, 1984.*
Bhattacharya–Chatterjee M. (2001) "The anti–idiotype vaccines for immunotherapy"; *Curr. Opinion. Mol. Ther.* Feb.;3(1):63–69.
Chang, K. et al.(1992) "Characterization of the Antigen (CAK1) Recognized by Monoclonal Antibody K1 Present on Ovarian Cancers and Normal Mesothelium"; *Cancer Research* 52:181–186.
Chang, K. et al. (1996) "Molecular cloning of mesothelin, a differentiation antigen present on mesothelium, mesotheliomas, and ovarian cancers"; *Proc. Natl. Acad. Sci. USA* 93:136–140.
Chang, K. et al. (1994) "Molecular Cloning and Expression of a cDNA Encoding a Protien Detected by the K1 Antibody from an Ovarian Carcinoma (OVCAR–3) Cell Line"; *Int. J. Cancer* 57:90–97.
Cho, et al. (2002) "Monoclonal antibody to a cancer–specific and drug–responsive hydroquinine (NADH) oxidase from the sera of cancer patients"; *Caancer Immunol. Immunother.* 51(3):121–129.

(Continued)

*Primary Examiner*—Larry R. Helms
*Assistant Examiner*—David J. Blanchard
(74) *Attorney, Agent, or Firm*—Greenlee, Winner & Sullivan, P.C.

(57) ABSTRACT

Compositions and methods for diagnosis of neoplastic tissue are described. Monoclonal antibodies which specifically recognize the tumor cell specific NADH:protein thiol reductase and the hybridoma cell lines which produce them are provided. Also provided are diagnostic and immunohistological assays for the identification of cells that are neoplastic.

1 Claim, 12 Drawing Sheets-

OTHER PUBLICATIONS

Chueh, P-J. et al. "A 33.5-kDa heat-and protease-resistant NADH oxidase inhibited by capsaicin from sera of cancer patients"; (Jun. 1997) *Arch. Biochem. Biophys.* 342(1):38-47.

Dillman, R.O. (2001) "Monoclonal Antibodies in the Treatment of Malignancy: Basic Concepts and Recent Developments"; *Cancer Invest.*19(8):833-841.

Durrant et al. (2001) "Human anti-idotypic antibodies can be good immunogens as they target FC receptors on antigen-presenting cells allowing efficient stimulation of both helper and cytotoxic T-cell responses"; *Int. J. Cancer* 1;92(3):414-420.

Harlow, et al. (1988) "Monoclonal Antibodies"; Cold Spring Harbor Chapter 6, pp. 148-155.

Kelker et al. (2001) "Cancer isoform of a tumor-associated cell surface NADH oxidase (tNOX) has properties of a prion"; *Biochemistry* Jun. 26;40(25):7351-7354.

Morré, D.J. (1995) "NADH oxidase activity of HeLa plasma membranes inhibited by the antitumor sulfonylurea"; *Biochim. Biophys. Acta* 1240:201-208.

Morré et al. (1995) "Capsaicin inhibits preferentially the NADH oxidase and growth of transformed cells in culture"; *Proc. Natl. Acad. Sci. USA* 92:1831-1835.

Morré et al. (1995) "Identification of antitumor sulfonylurea binding proteins of HeLa plasma membranes"; *Biochim. Biophys. Acta* 1236:237-243.

Morré et al. (1995) "The antitumor sulfonylurea N-(4-methylphenylsulfonyl)-N'-(4-chlorophenyl) urea (LY181984) inhibits NADH oxidase activity of HeLa plasma membranes"; *Biochim. Biophys. Acta* 1240:11-17.

Morré et al. (1996) "Antitumor sulfonylurea-inhibited NADH oxidase of cultured HeLa cells shed into media"; *Biochim. Biophys. Acta* 1280:197-206.

Morré et al. (1996) "Capsaicin Inhibits Plasma Membrane NADH Oxidase and Growth of Human and Mouse Melanoma Lines"; *Eur. J. Cancer* 32:1995-2003.

Morré et al. (1997) "NADH Oxidase Activity from Sera Altered by Capsaicin Is Widely Distrubted among Cancer Patients"; *Arch Biochem. Biophys.* 342:224-230.

Morré et al. (1999) "Use of dipyridyl-dithio substrates to measure directly the protein disulfide-thiol interchange activity of the auxin stimulated NADH: protein disulfide reductase (NADH oxidase) of soybean plasma membranes"; *Mol. Cell. Biochem.* Oct;200(1-2):7-13.

Morré and Morré (1995) "Differential Response of the NADH Oxidase of Plasma Membranes of Rat Liver and Hapatoma and HeLa Cells to Thiol Regents"; *J. Bioenerg. Biomemb.* 27:137-144.

Morré and Reust (1997) "A Circulating Form of NADH Oxidase Activity Responsive to the Antitumor Sulfonylurea N-4-(methylphenylsulfonyl)-N'-(4-chlorophenylurea (LY181984) Specific to Sera from Cancer Patients"; *J. Biomemb. Bioenerg.* 29:281-289.

Paulik et al. (1999) "Drug-antibody conjugates with anti-HIV activity"; *Biochem. Pharmacol.* Dec. 1;58(11):1781-1790.

Wilkinson et al. (1996) "Isolation and Identification of a Protein with Capsaicin-Inhibited NADH Oxidase Activity from Culture Medic Conditioned by Growth of HeLa Cells"; *Arch. Biochem. Biophys.* 336:275-282.

Yantiri and Morré (2001) "Isolation and characterization of a tumor-associated NADH oxidase (tNOX) from the HeLa cell surface"; *Arch Biochem. Biophys.* Jul. 15:391(2):149-159.

\* cited by examiner

MONOCLONAL ANTIBODIES SPECIFIC FOR NEOPLASIA-SPECIFIC NADH:DISULFIDE REDUCTASE

CROSS REFERENCE TO RELATED APPLICATIONS

This application claims benefit of U.S. Provisional Application 60/359,070, filed Feb. 22, 2002, which is incorporated by reference herein to the extent there is no inconsistency with the present disclosure.

ACKNOWLEDGMENT OF FEDERAL RESEARCH SUPPORT

Not applicable.

THE BACKGROUND OF THE INVENTION

The invention relates generally to monoclonal antibodies specific for a neoplasia marker, specifically NADH:protein disulfide reductase, to cell lines producing those neoplastic marker-specific monoclonal antibodies and immunological assays and to diagnostic methods using those monoclonal antibodies and to substantially purified NADH:protein disulfide reductase which is characteristic of transformed cells and/or neoplastic cells or tissue. Because the antibodies specifically prevent the growth of cancer cells, induce apoptotic cell death of cancer cells, without effect on normal cells, the described monoclonal antibodies are useful for inhibiting cancer cell growth and for treating a neoplastic condition.

Our laboratory has described an activity of the HeLa cell plasma membrane that catalyzes the reduction of protein disulfide bonds at the expense of NADH. Measured as an NADH oxidase or NADH:protein disulfide reductase (PDR), the protein in the absence of NADH exhibits a protein disulfide-thiol interchange (TIP) activity. In HeLa cells the ability of plasma membrane vesicles to oxidizes NADH is partially inhibited by the quinone site inhibitor capsaicin (8-methyl-N-vanillyl-6-noneamide) and the antitumor sulfonylurea LY181984. The latter appears to correspond to a 34 kD sulfonylurea binding protein that is exposed at the external surface of the cells and eventually shed into culture media [Wilkinson et al. (1996) *Arch. Biochem. Biophys.* 336:275–282]. A corresponding capsaicin-[Morré et al. (1997) *Arch. Biochem. Biophys.* 342:224–230] or sulfonylurea-[Morré and Reust (1997) *J. Biomemb. Bioenerg.* 29:281–289] inhibited activity is found in sera of cancer patients. Plasma membranes isolated from non-transformed cells or sera from healthy individuals appear to lack entirely the drug inhibited activity [Morré et al. (1995) *Proc. Natl. Acad. Sci. USA* 92:1831–1835]. Whereas plasma membrane vesicles isolated from both normal and transformed cells exhibit an NADH oxidase activity, only the NADH oxidase activity of plasma membrane vesicles from transformed cells and the shed form from sera of cancer patients are inhibited by capsaicin and the antitumor sulfonylurea.

SUMMARY OF THE INVENTION

The present invention provides monoclonal antibodies specific for a neoplasia marker, specifically NADH:protein disulfide reductase also known as tNOX, cell lines producing those neoplastic marker-specific monoclonal antibodies, as well as immunological assays using biological samples from the human or animal in need of the detection of a neoplastic condition, imaging procedures used in the human or animal and diagnostic methods using those monoclonal antibodies. A neoplastic condition can also be detected by the specific inhibition of protein disulfide reductase activity or of NADH oxidase activity by the monoclonal antibodies of the present invention in a enzymatic activity. The monoclonal antibodies of the present invention specifically bind with the neoplastic marker, either on the surfaces of neoplastic cells, in serum or other biological samples and to the tNOX protein which has been bound to a solid support, for example, after resolution from other proteins by gel electrophoresis, especially sodium dodecyl sulfate polyacrylamide gel electrophoresis, or other protein separation techniques. In method of detection, the tNOX-specific monoclonal antibodies are desirably bound with a detectable marker such as an enzyme, a fluorescent compound, a radionuclide or other detectable label known to the art. Alternatively, the binding of the monoclonal antibody can be detected in a sandwich assay, where a second antibody specific for the mouse monoclonal antibody is labeled with a detectable marker, as known to the art. A specifically exemplified hybridoma cell line producing monoclonal antibodies specific for the tNOX neoplasia-specific marker is hybridoma cell line 12.1.

The present invention further provides therapeutic compositions comprising the monoclonal antibodies of the present invention and a pharmaceutically acceptable carrier, and therapeutic methods for treating neoplastic conditions in humans and animals using these therapeutic compositions. The monoclonal antibodies of the present invention inhibit the growth of and induce apoptosis in neoplastic cells, including cancer cells.

The hybridoma cell line which produces monoclonal antibody MAB 12.1 has been deposited with the American Type Culture Collection, Manassas, Va., 20108 on Apr. 4, 2002, under the terms of the Budapest Treaty. This deposit is identified by Accession No. ATCC PTA-4206. The deposit material is from a sample maintained by applicants since prior to the filing date of U.S. Provisional Application 60/359,070. The deposit will be maintained in the ATCC depository for a period of 30 years, or 5 years after the most recent request, or for the effective life of the patent, which ever is longer, and will be replaced if the deposit becomes non-viable during that period.

BRIEF DESCRIPTION OF THE DRAWINGS

FIG. 4 illustrates the growth of HeLa cells in the absence (none) and presence of mouse ascites containing MAB 12.1 directed to tTIP of human serum at dilutions of 1:100 and 1:1000. The solid line is the cell number of the initial inoculum. Not only was growth reduced, but all cells were dead at both dilutions of antisera by 168 h. Results with MAB 12.5 were similar.

DETAILED DESCRIPTION OF THE INVENTION

Figure 1:
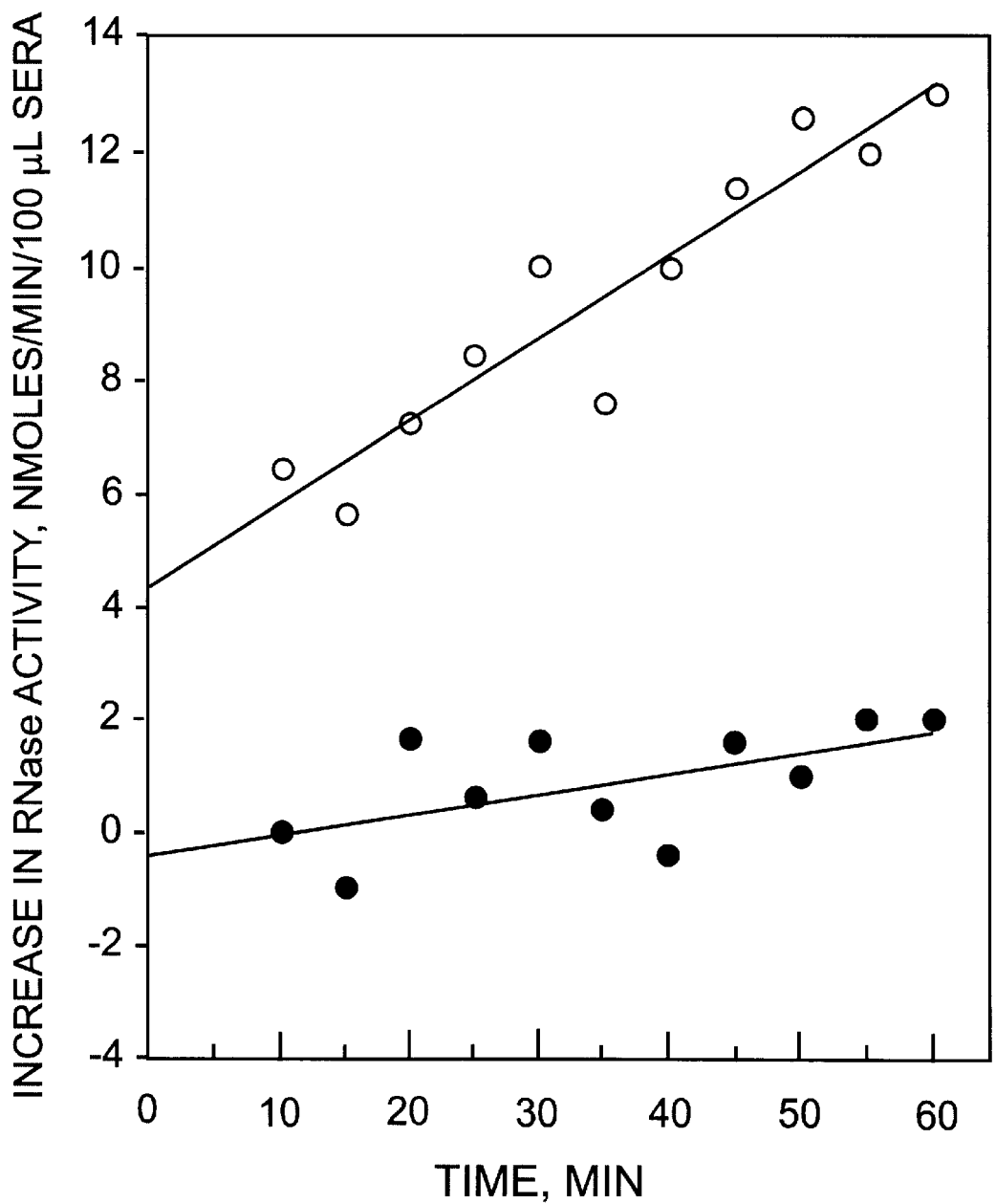
FIG. 1 shows the inhibition by monoclonal antibody 12.1 at a 1:1000 dilution of the protein disulfide-thiol interchange activity specific to sera of cancer patients as determined by restoration of activity to scrambled and inactive ribonuclease A (closed circles). For comparison, activity in the absence of tNOX-specific antibody is also shown (open circles).

As used herein, neoplasia (or neoplastic disorder) describes a disease state of a human or an animal in which there are cells and/or tissues which proliferate abnormally. Neoplastic conditions include, but are not limited to, cancers, sarcomas, tumors, leukemias, lymphomas, and the like. The cell surface, neoplastic cell specific (tumor specific) NADH oxidase/protein disulfide-thiol interchange protein (tNOX) is characteristic of neoplastic cells and tissue as well as virus-infected cells (for example, human immunodeficiency virus, feline immunodeficiency virus, etc).

A biological sample, as used herein, can be a cell culture sample, a portion of tumor tissue, a biopsy specimen including but not limited to a needle biopsy specimen, peritoneal fluid, lung fluid, other bodily fluid, serum, blood, urine, semen, mucosal secretion, cells, tissue, bone marrow, Pap smear, among others. The sample, after collection, can be frozen before analysis, or it can be immediately prepared for diagnostic analysis. The sample can be a paraffin-embedded sample.

In the present report we describe the generation of a monoclonal antibody specific for tumor specific (i.e., neoplastic cell specific) NADH oxidase (tNOX) protein disulfide reductase (PDR) activity. The antigen used in the preparation of the monoclonal antibodies of this invention was the shed form of tNOX isolated from pooled sera of human cancer patients. The antisera which appear to be directed to the capsaicin binding region of the cancer-specific molecule specifically inhibit growth of transformed cells and as shown by immunolocalization, react with the cell surface of HeLa cells and with the surface of human cancer in situ but not with surrounding stromal tissues.

Pooled sera of cancer patients contained an NADH oxidase that was inhibited 20 to 30% by capsaicin at a final concentration of 1 to 100 μM. NADH oxidation by pooled sera from normal patients was not inhibited over the same range of capsaicin concentrations. The property of capsaicin inhibition was utilized to monitor the isolation and purification of the capsaicin-inhibited activity from cancer patient sera. The activity was characterized previously as to cofactor requirements, sensitivity to thiol reagents and conditions for assay [Morré et al. (1995) *Biochim. Biophys. Acta* 1236:237–243; Morré et al. (1995) *Biochim. Biophys. Acta* 1240:11–17; Morré et al. (1995) *Proc. Natl. Acad. Sci. USA* 92:1831–1835; Wilkinson et al. (1996) *Arch. Biochem. Biophys.* 336:275–282; Morré et al. (1996) *Biochim. Biophys. Acta* 1280:197–206; Morré et al. (1996) *Eur. J. Cancer* 32:1995–2003; see also U.S. Pat. No. 5,569,673]. The tNOX protein is identified by its amino acid sequence, which is disclosed in WO 01/32673.

tNOX, a cancer specific activity of plasma membranes and sera of cancer patients, was initially defined as an activity based on oxidation of NADH that was responsive to certain anticancer drugs, including the anticancer sulfonylureas and the vanilloids capsaicin and vanillylamine. The detection was complicated by a second activity, which is neither cancer specific nor responsive to anticancer drugs, designated CNOX (cell NADH oxidase of normal cells).

Two developments allow detection of tNOX, at least in sera, without significant interference from other forms of NOX using procedures not dependent on drug sensitivity for tNOX identification.

A tNOX-specific protein disulfide-thiol interchange (tTIP) activity is unique to sera from cancer patients. The activity is not detectable in sera from normal patients or in sera from patients with disorders other than cancer. The serum tNOX restores the activity of scrambled, inactive ribonuclease and the scrambled, inactive forms of trypsin and β-galactosidase via its protein disulfide reductase activity. tNOX also cleaves the tTIP-specific substrate (DTNA).

Monoclonal antibodies MAB 12.1 and MAB 12.5 as identified herein react specifically with tNOX monomers in cancer sera and do not react with proteins in normal sera.

Two mice were immunized and boosted with 34 kD tNOX purified from pooled cancer patient sera. Fusions carried out with the second mouse yielded two tNOX-specific monoclonal antisera. Primary screening of hybridomas was with 34 kD tNOX partially purified from HeLa cells (Cellex, now BioVest Minneapolis, Minn.). Secondary screening was based on high affinity binding to tNOX, resulting in complete inhibition of tNOX (but not CNOX) activity in patient sera. The clones chosen after this screening regimen generated antisera that blocked NOX activity inhibited by capsaicin or antitumor sulfonylurea in sera of cancer patients, but the antisera were without effect on NOX activity in the sera collected from normal volunteers. Two hybridoma cell lines were obtained and designated 12.1 and 12.5. Both produced antibodies in mouse ascites and were very similar, if not identical, in their properties. MAB 12.1 has been more extensively characterized.

Figure 2:
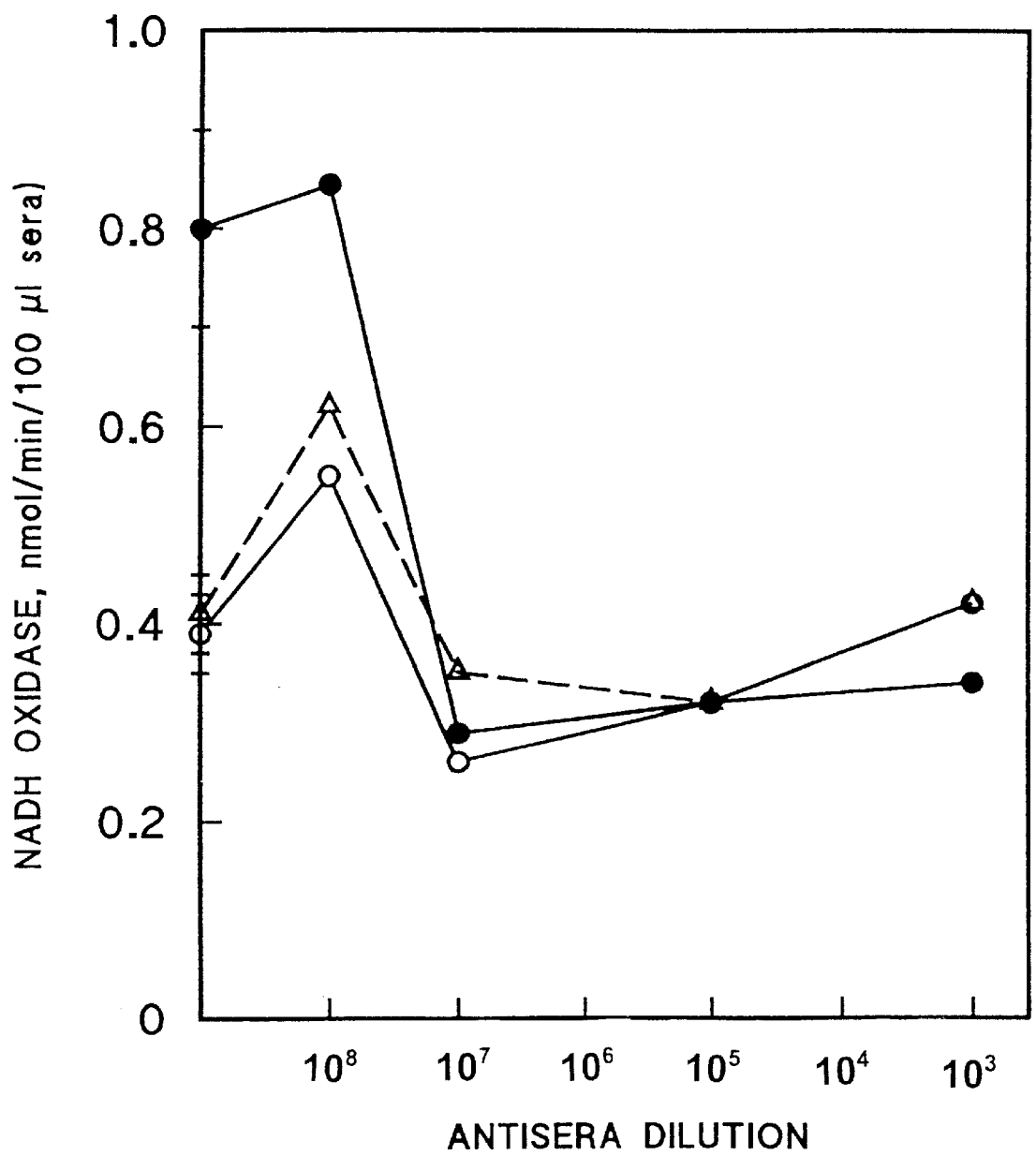
FIG. 2 shows dilution of 12.1 ascites monoclonal antibody preparations to estimate affinity for inhibition of capsaicin-inhibited NADH oxidase activity (solid symbols—no capsaicin; open circles—1 µM capsaicin. Capsaicin-responsive NADH oxidase was blocked by the antisera at dilutions of up to $1:10^7$. The antibody preparations were without effect on NADH activity of sera from normal volunteers.
Figure 3:
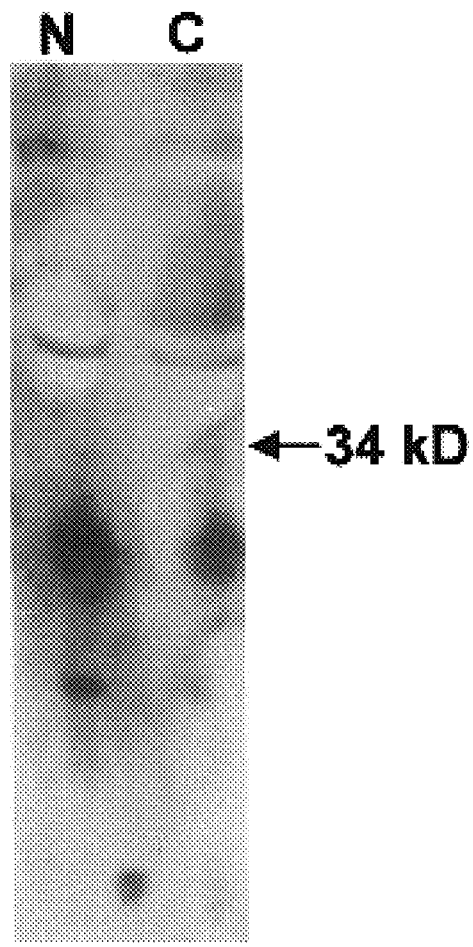
FIG. 3 shows Western blot with ECL detection comparing pooled sera from healthy volunteers (N) and pooled sera from cancer patients (C) using MAB 12.5. Results with MAB 12.1 were similar. The antibody source was mouse ascites. A purified IgG fraction was used. The antisera detect an approximately 34 kD (33.5 kD) band previously associated with tNOX activity (arrow).
Figure 4:
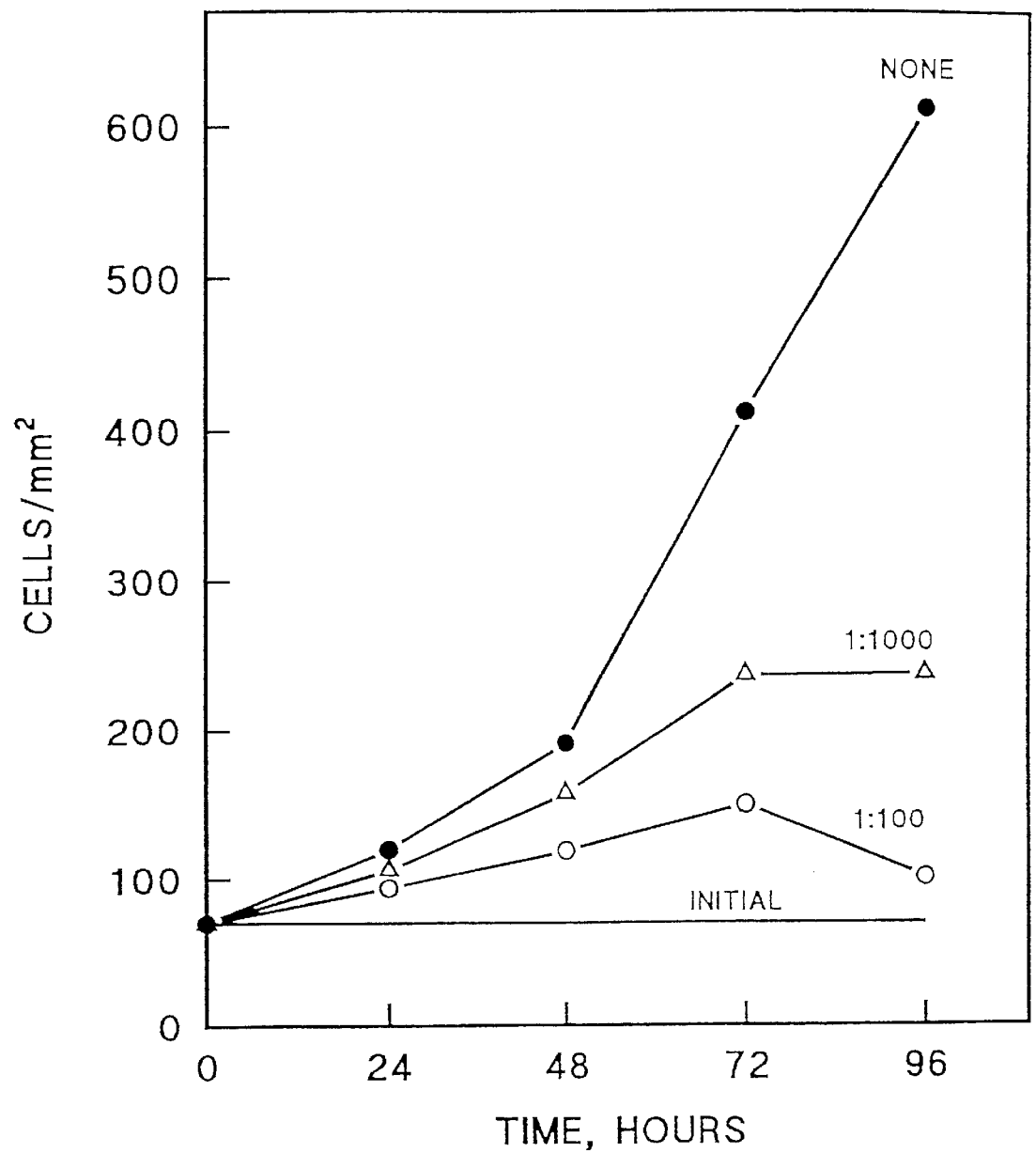
Figure 5:
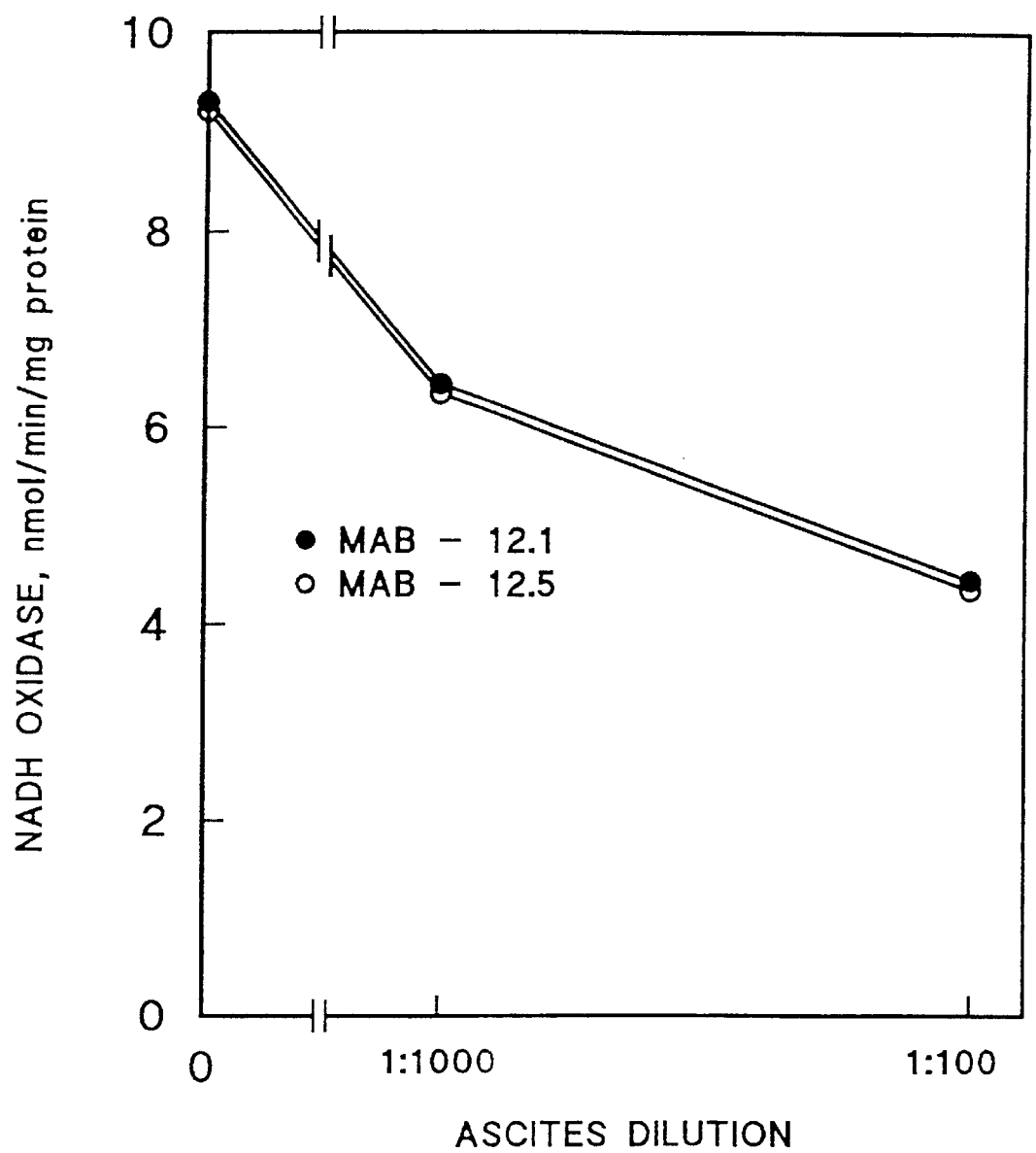
FIG. 5 shows MAB inhibition of tNOX activity of plasma membrane vesicles isolated from mouse myeloma SP-2, the mouse myeloma line used for generation of the hybridomas producing MAB 12.1 and MAB 12.5. Both antisera (mouse ascites) inhibited at 1:1000 and 1:100.

MAB 12.1 inhibits NOX activity from cancer patient sera to the same extent as capsaicin (Table 1), i.e. tNOX activity, as defined above, is inhibited. The activity in sera of cancer patients not inhibited by capsaicin (CNOX) is not inhibited by MAB 12.1 or MAB 12.5 (see also Table 1). These monoclonal antibody preparations are without effect on thiol interchange or NADH oxidase activities in the sera of normal volunteers (Table 1). Serotyping demonstrates the MAB 12.1 cell line produces IgG, and these antibodies are immunoprecipitated by reaction with tNOX (Table 2). When generated as mouse ascites, each monoclonal antibody preparation blocks tNOX (and tTIP) activities at a dilution of $1 \times 10^7$ and appears to be of high affinity (FIG. 2). These antibodies react on Western blots with the 34 kD protein component previously associated with tNOX activity (FIG. 3). The 34 kD band may represent a dimer of two subunits stabilized by strong hydrophobic interactions. The antisera slow the growth and eventually kill HeLa cells (FIG. 4). Most effective are the mouse ascites, presumably through complement-mediated cell killing (cells grown in heat-treated sera). At the antibody dilution of 1:1000, the cells grew slowly, even from the beginning of the experiment and, at about 72 h, began to undergo apoptotic cell death (FIG. 4). At an antibody dilution of 1:1000, the cells also grew slowly, stopped growing between 72 and 96 h and then began to die. Within a further 48 h, these cells also were dead. The pattern of growth inhibition paralleled that of the antitumor sulfonylureas, but the antibodies were far more effective in inducing apoptotic cell death than the sulfonylureas, even when the sulfonylureas were tested at concentrations approaching their solubility limits in culture media. Control ascites (tubulin as antigen) generated in parallel and in the same strain of mice, resulted in only a small inhibitory response as compared with the effects of ascites fluid from MAB 12.1 or MAB 12.5. Control ascites without antigen were without effect on growth in cell culture. Monoclonal antisera (no ascites) in the absence of complement inhibited the growth of cells but did not result in massive cell killing. Results were similar to those previously observed with polyclonal tNOX antisera.

tNOX activity of plasma membranes isolated from mouse myeloma cells (FIG. 5) and growth of mouse myeloma cells (Table 3) also were inhibited by the 12.1 and 12.5 monoclonal antibody preparations. The producing myeloma cells grow slowly and die if antibody titers reach critical levels.

Figure 6A:
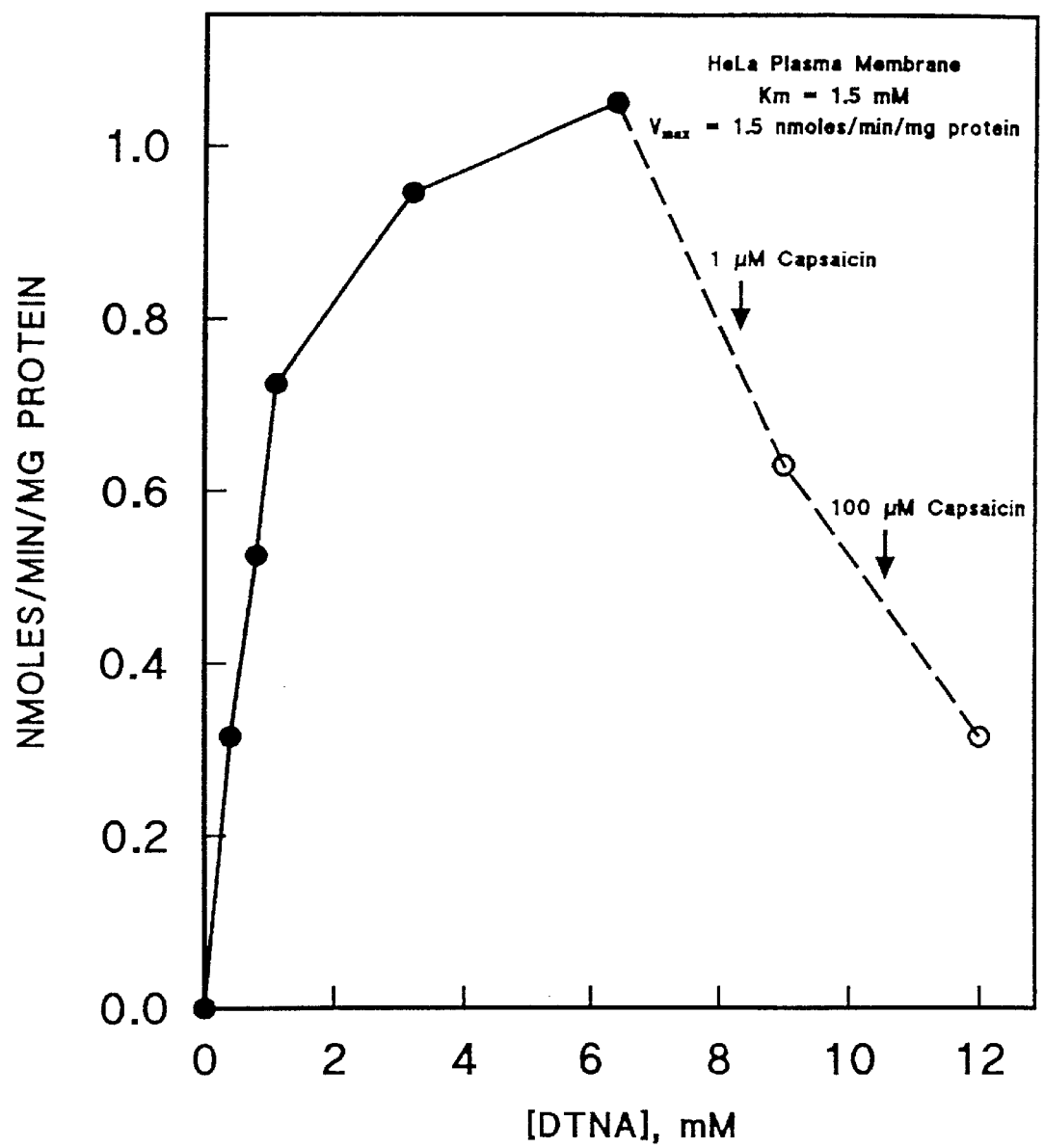
FIG. 6A reflects a direct assay of cancer-specific tTIP activity of HeLa plasma membranes using 6,6'-dithionicotinic acid (DTNA) substrate. Similar results were obtained with sera of cancer patients. The activity showed typical saturation kinetics with respect to substrate with a Km of 1.5 mM; the $V_{MAX}$ is estimated as 1.5 nmoles/min/mg protein. With normal sera no substrate-dependent activity was observed.

When tNOX activity was measured using the tTIP-specific substrate DTNA, MAB 12.1 acted as a competitive inhibitor with both plasma membranes from HeLa cells (FIG. 6A) and cancer patient sera. Inhibition by the antibody can be reversed in the presence of high substrate concentrations, indicating that the epitope to which the cancer-specific antibody is directed is the catalytic site of the protein disulfide-thiol interchange activity of tNOX. It is this portion of the tNOX protein where the characteristics unique to cancer are most obvious and will yield cancer-specific antisera. The screening procedure was designed to select for such an epitope. NADH also competes with the cancer-specific monoclonal antibody preparations, but the competition is uncompetitive (Table 4), indicating that antibody and NADH bind at different sites on the enzyme.

Figure 6B:
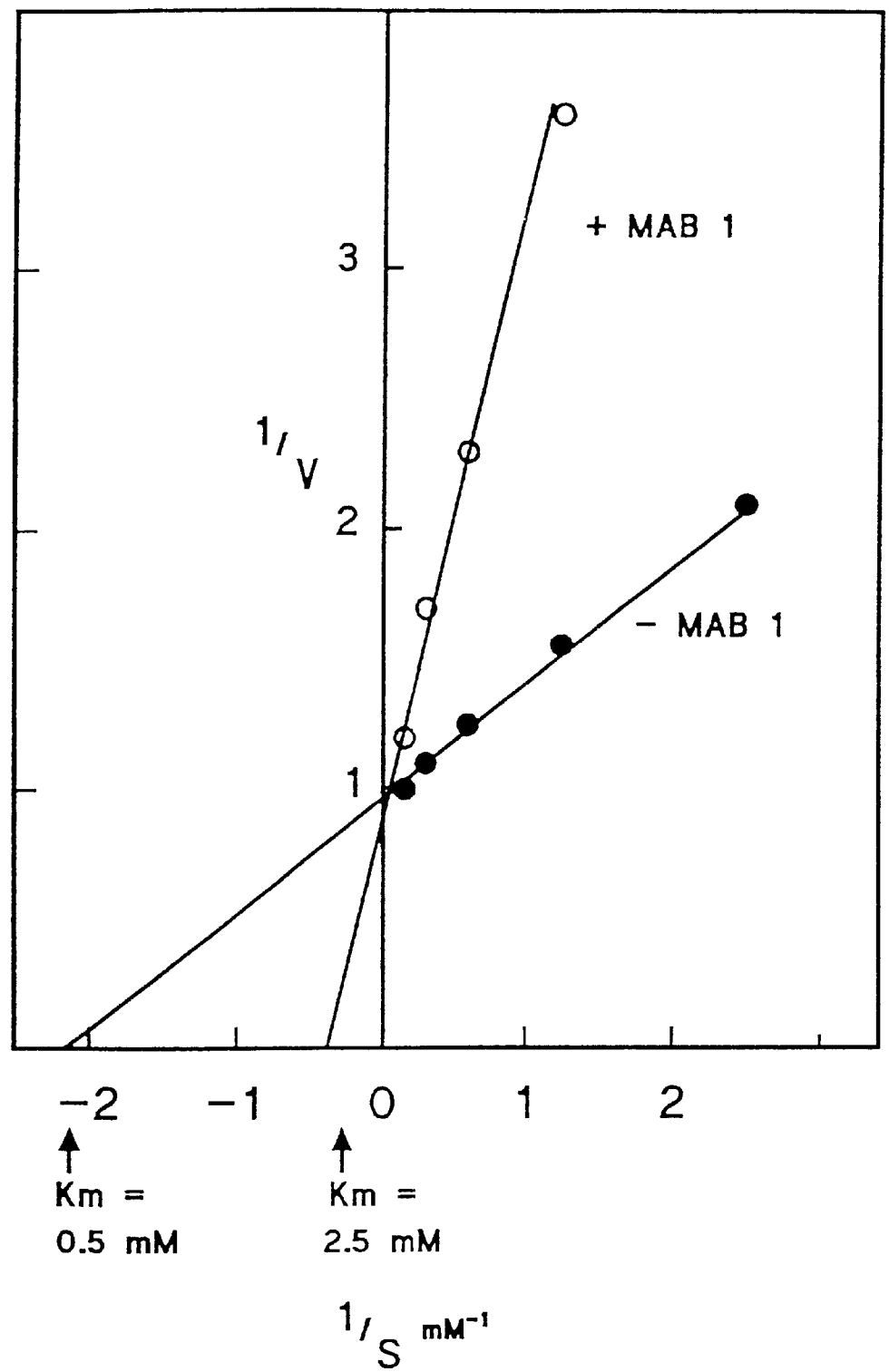
FIG. 6B shows a Lineweaver-Burke double reciprocal kinetic analysis of direct assay in the presence and absence of MAB 12.1 (MAB 1). In the presence of the monoclonal antisera, the apparent Km was shifted to higher substrate concentrations (2.5 mM from 0.5 mM) but the maximum velocity was unaffected (same ordinate intercept for both plus and minus antibody) indicative of competitive inhibition for the substrate site.
Figure 7:
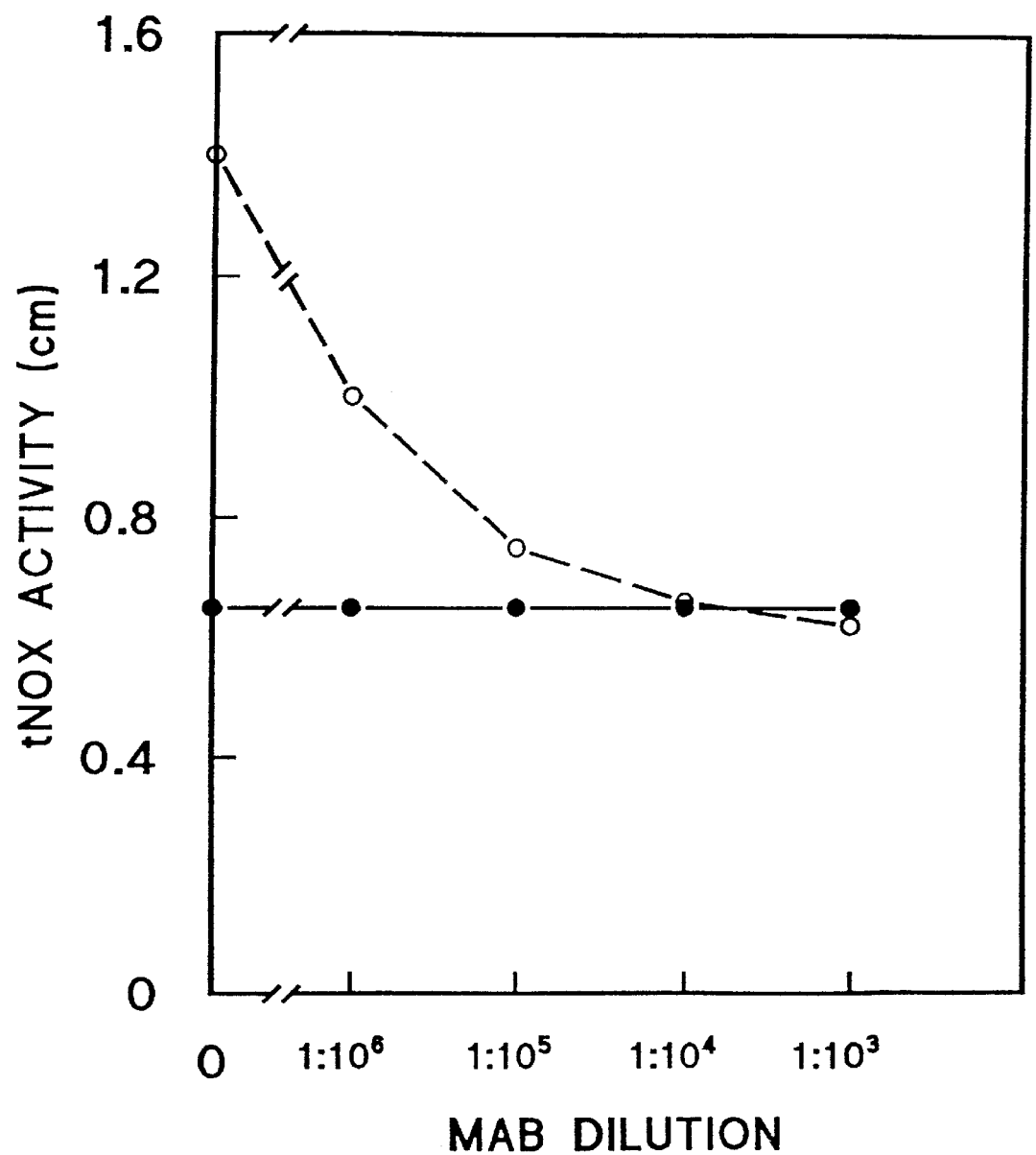
FIG. 7 is an illustration of the inhibition of NOX activity by MAB 12.5 of plasma membrane vesicles isolated from BT-20 mammary adenocarcinoma cells (open circles) and lack of response of plasma membrane vesicles from MCF-10H mammary epithelial (non-malignant) cells (closed circles).

With the new tNOX-specific substrate, the kinetics indicate simple competitive inhibition (shift in Km to higher substrate concentration and no change in the apparent Vmax) (FIG. 6B, Table 4).

The mouse MAB 12.1 and MAB 12.5 ascites preparations are without effect on growth of 3T3 mouse fibroblast cells and WI-38 human diploid fibroblast cells.

Figure 8:
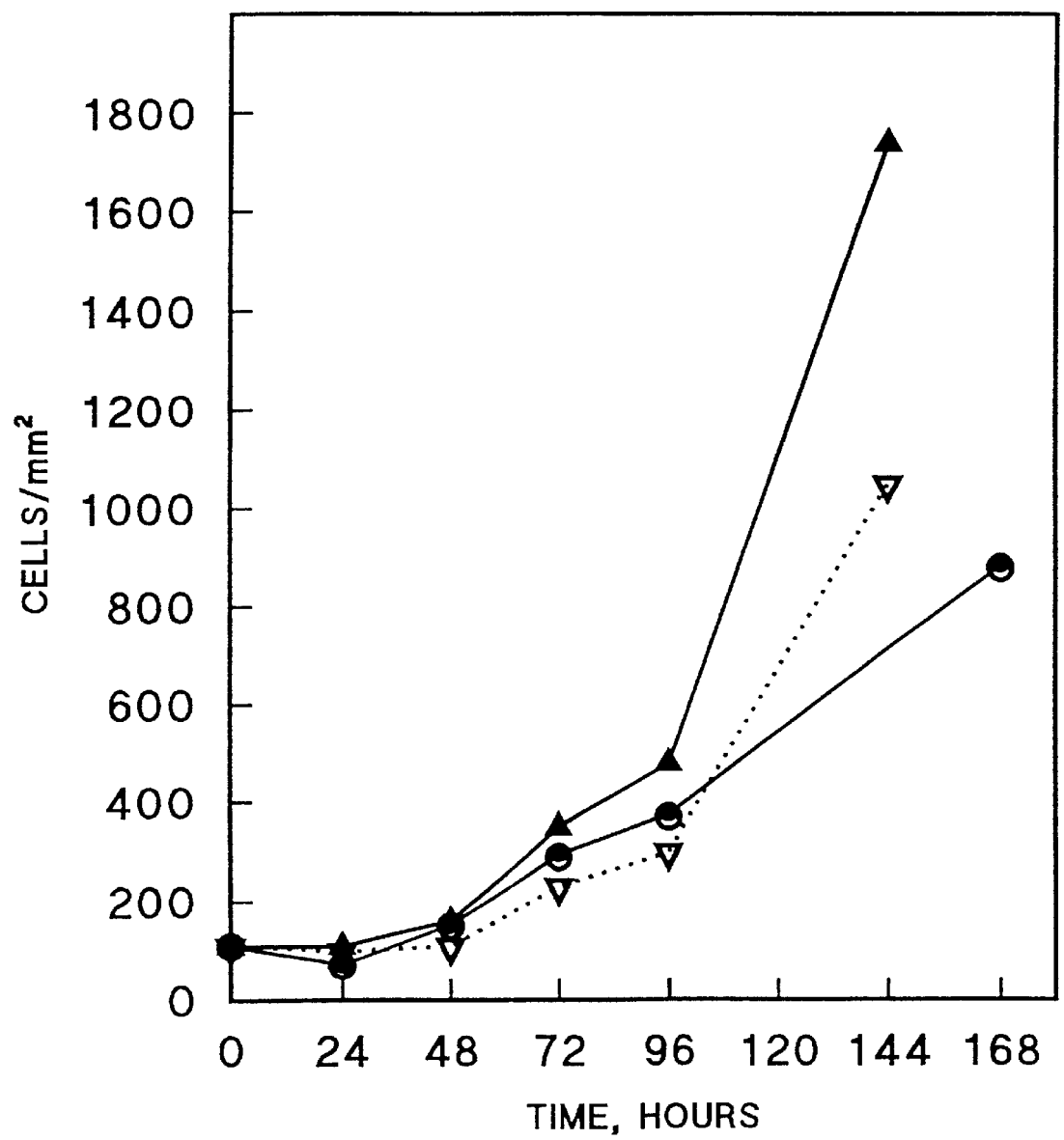
FIG. 8 shows the growth of BT-20 adenocarcinoma in the presence (▽) or absence (▲) tNOX-specific of monoclonal antibody at a dilution of 1:10,000. The growth of MCF 10A mammary epithelial cells was the same in the presence or absence of tNOX-specific antibodies (◉).

The 12.1 and 12.5 monoclonal antibodies inhibit tNOX activity (FIG. 8) and growth (Table 6) of human mammary adenocarcinoma cells in culture (BT-20), but they do not inhibit CNOX activity or growth of non-malignant mammary epithelial cells (MCF 10 A adenoma) (FIG. 8).

Figure 9A:
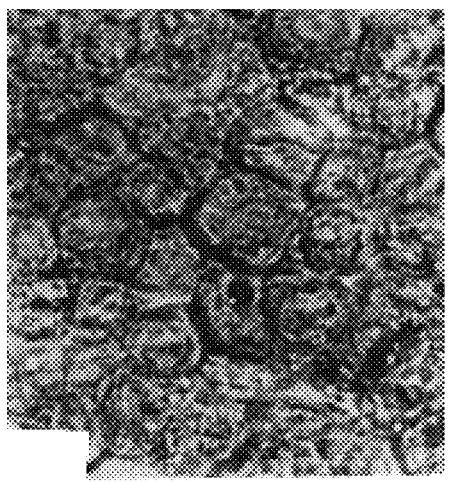
FIGS. 9A–9D illustrate the immunocytochemistry of formalin-fixed (10% neutral formalin) and paraffin-embedded HeLa cells (FIGS. 9A–9B) and human renal carcinoma cells (FIGS. 9C–9D) reacted with affinity purified IgG from culture media of 12.1 hybridoma grown in a CELLMAX system. Deparaffinized slides were hydrated, treated five minutes with hydrogen peroxide and carried through an antigen retrieval protocol. Tissue sections were covered with normal goat serum followed by MAB diluted 1:10 (positive tissue sections +) or Tris buffer negative tissue sections −). Slides were incubated one hour either at room temperature (RT) or at 37°(heat). After incubation, Super sensitive MultiLink was added (5 mm.) followed by Super Sensitive Label (5 mm.). Alkaline phosphatase-conjugated streptavidin was used for slides being stained with new fuchsin (NF). After rinsing, slides were developed with the appropriate chromogen/substrate solution. Magnification× 1000.
Figure 9B:
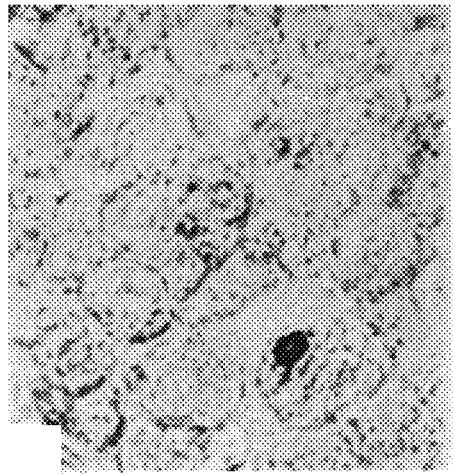
Figure 9C:
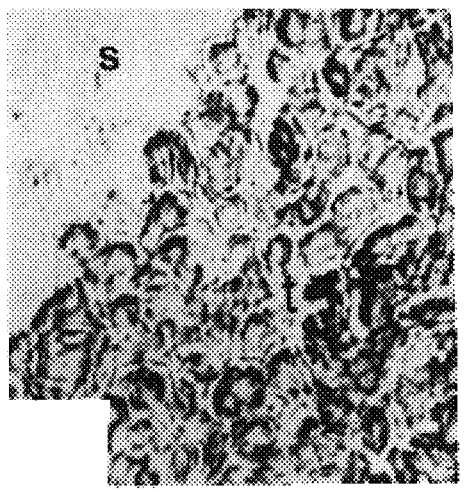
Figure 9D:
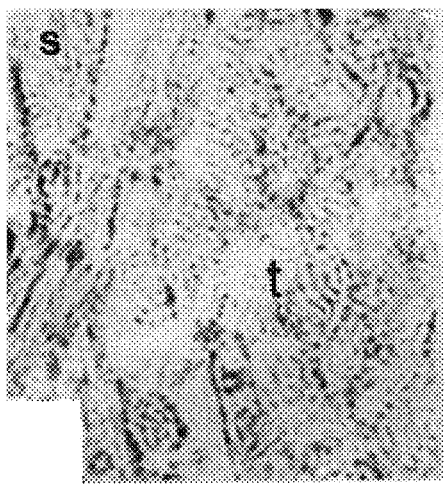
Figure 10:
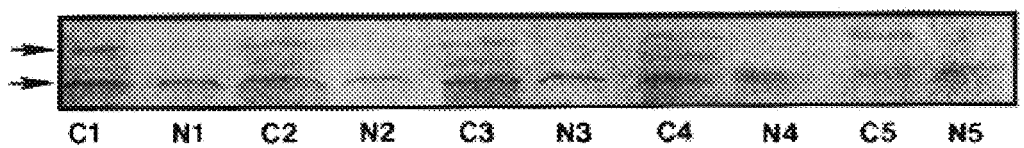
FIG. 10 shows the results of Western blot analysis of freshly collected crude sera of cancer patients (C) and from health volunteers (N) with tNOX-specific antibody after SDS-PAGE. Each lane was loaded with 1 μl of sera. A cancer-specific band was observed at ca. 33.5 kD (arrows). Sera were first delipidated with Cleanascite (CPG, Lincoln Park, N.J.) and treated with proteinase K (200 μg/ml for 2 h at 37° C. followed by heating to 70° C. for 20 min to inactivate proteinase K). Cancers represented were: prostate (C1, lymphoma (C2), ovarian (C3), leukemia (C4) and breast (C5). N1 to N5: sera from healthy volunteers. The common band at ca. 29 kDa (lower arrow) was proteinase K which cross-reacts unspecifically with mAb 12.1 at the large amounts of proteinase K added to provide an index of uniformity of loading. Reactive bands were also visible in samples prepared without the delipidation and protease steps.
Figure 11:
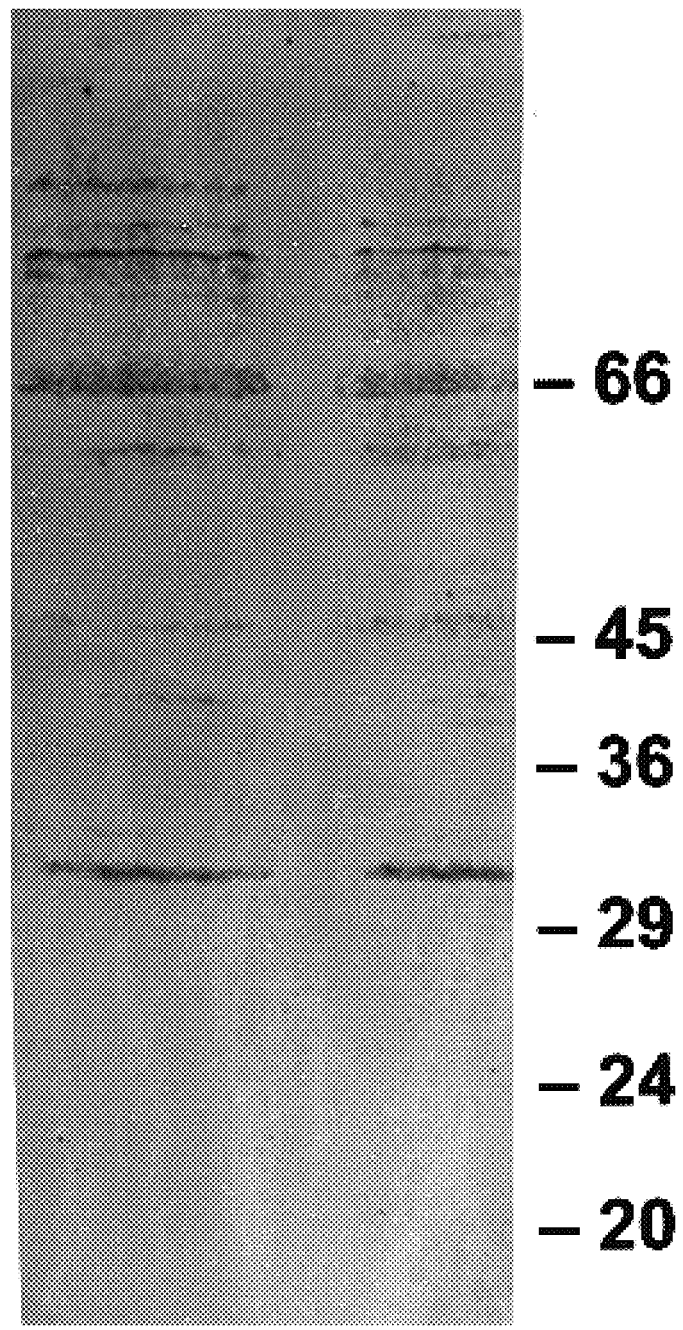
FIG. 11 shows the results of HeLa cell plasma membrane proteins separated by SDS-PAGE and transferred to PVDF for Western blot analysis with tNOX-specific antibody. MAB 12.1 reacts with the tNOX monomer (c) at 34 kD, the dimer (b) at 68 kD and a putative heterotetramer (a) at 85 kD of the tNOX dimer, plus a 17 kD component.

MAB 12.1, when contacted with paraffin-embedded and sectioned HeLa cells or human renal carcinoma cells, binds to the cell surface as detected by avidin-linked alkaline phosphatase (new fuchsin substrate, Bio-Genex, San Ramon, Calif.) or horseradish peroxidase (diaminobenzidine substrate) (FIG. 9A). The cytoplasm and nuclei were not stained. There was no significant signal in the absence of 12.1 MAB (FIG. 9B).

MAB 12.1, when presented to paraffin-embedded pathological specimens of renal, colon and ovarian cancers, reacted with the borders of the cancer cells but not with surrounding stromal cells. There was no significant signal in the absence of the tNOX-specific monoclonal antibodies.

In a series of reports, our laboratory has described an antitumor sulfonylurea and capsaicin-responsive oxidation of NADH associated with plasma membranes of HeLa and other transformed cell lines [Morré et al. (1995) *Biochim. Biophys. Acta* 1236:237–243; Morré et al. (1995) *Biochim. Biophys. Acta* 1240:11–17; Morré et al. (1995) *Proc. Natl. Acad. Sci. USA* 92:1831–1835; Wilkinson et al. (1996)

supra; Morré et al. (1996) *Biochim. Biophys. Acta* 1280:197–206; Morré et al. (1997) *Eur. J. Cancer* 32:1995–2003]. The activity is at the external cell surface and, as is characteristic generally of ectoproteins of the cell surface [Morré, D. J. (1995) *Biochim. Biophys. Acta* 1240:201–208], the protein is shed into culture medium (Wilkinson et al. (1996) supra; Morré et al. (1996) *Biochim. Biophys. Acta* 1280:197–206].

An NADH oxidase activity, also responsive to inhibition or stimulation by capsaicin was observed as well with sera of cancer patients [Morré et al. (1997) *Arch. Biochem. Biophys.* 342:224–230]. This activity has been characterized with respect to conditions of assay and sensitivity to thiol reagents. This activity parallels the corresponding activities of HeLa plasma membrane [Morré and Morré (1995) *J. Bioenerg. Biomemb.* 27:137–144] and of culture media conditioned by the growth of HeLa cells [Wilkinson et al. (1996) *Arch. Biochem. Biophys.* 336:275–282]; Morré et al. (1996) *Biochim. Biophys. Acta* 1280, 197–206]. Under the oxidizing conditions employed for assay, the dominant response was that of inhibition with sera of individual cancer patients. In a small number of patient sera (6%), capsaicin stimulated at either 1 or 100 μM. With the pooled sera samples of the present study, a capsaicin inhibition of 20 to 30% was observed, which is near the average inhibition observed with sera from individual cancer patients.

A shed 33.5 (34) kD protein with capsaicin- or antitumor sulfonylurea-inhibited NADH oxidase activity has been isolated from cell culture media conditioned by growth of HeLa cells [Morré et al. (1995) *Biochim. Biophys. Acta* 1239:237–243; Wilkinson et al. (1996) supra]. Polyclonal antisera raised against this protein inhibited and immunoprecipitated the capsaicin-inhibited NADH oxidase activity, providing further confirmation that the drug-responsive NADH oxidase activity is associated with the 33.5 kD component.

In the present study, the corresponding activity was purified from sera of cancer patients and used as an immunogen to raise monoclonal antibodies. The monoclonal-antibody producing hybridoma clones selected, 12.1 and 12.5, produce monoclonal antibodies that appear to be specific for a 34 kD protein at the surface of cancer cells and shed into sera of cancer patients. The specificity of the antisera was confirmed by inhibition of activity, immunoprecipitation and Western blot analyses, as well as by kinetic analyses using dithio-dipyridyl substrates also inhibited by capsaicin, which showed that the antibodies served as classical competitive inhibitors of the capsaicin-inhibited activity. With NADH as substrate, activity also was inhibited, but the competition was uncompetitive.

Evidence demonstrates a role for the capsaicin-inhibited tNOX in growth. We examined the effects of MABs 12.1 and MAB 12.5 on the growth of transformed and non-transformed cells in culture. The present studies show the tNOX-specific monoclonal antibodies are remarkably efficient at disrupting the growth of HeLa and other transformed human and mouse cells. After several days of growth arrest, antibody-treated transformed cells underwent apoptotic cell death within 72 to 196 h.

Specificity of the cell killing was evident from comparisons of the response of MCF-1 OA mammary epithelial cells and BT-20 mammary adenocarcinoma cells. With the non-transformed MCF-1 OA cells, neither growth nor NADH oxidation by isolated plasma membrane vesicles was inhibited by the tNOX-specific MAB 12.1 at any dilution tested. However, antibody treatment of the transformed BT-20 cells strongly inhibited both NADH oxidase activity and cell growth.

We have previously shown that the BT-20 cells contain a constitutively activated component of NADH oxidase activity which is inhibited by capsaicin and is not present in the MCF-1 OA cells [Morré et al. (1995) *Proc. Natl. Acad. Sci. USA* 92:1831–1835]. The MAB-inhibited component of the BT-20 cells corresponds almost exactly to this previously described capsaicin-inhibited component.

Specificity is further indicated by the failure of ascites fluid generated in the absence of tNOX-specific antibody-forming cells to inhibit the growth of transformed cells. Ascites fluid comprising antitubulin-specific antibodies did not preferentially inhibit the growth of tumor cells in culture over nontransformed cells in culture.

Incubation at pH 5 resulted in the disappearance of the capsaicin-inhibited NADH oxidase from the surface of the treated HeLa S cells (Table 7) and its appearance in soluble form. tNOX was also released from plasma membrane vesicles by the pH 5 treatment. The recovery of plasma membrane NADH oxidase activity in the supernatant from the pH 5-treated cells was 81%.

More than 30 such preparations were prepared from HeLa cells and analyzed. Capsaicin inhibition of the NADH oxidase activity varied among preparations between 20 and 40% at 1 μM capsaicin and between 40 and 60% at 100 μM capsaicin. This variation was correlated with the relative proportion of the 34 kD protein present in the extracts.

The capsaicin-inhibited NADH oxidase is resistant to heating at 50° C. and to protease digestion. The sulfonylurea-[Morré et al. (1995) *Biochim. Biophys. Acta* 1240:11–17] and capsaicin-inhibited [Morré et al. (1995) *Proc. Natl. Acad. Sci. USA* 92:1831–1835] NADH oxidase from culture media conditioned by growth of HeLa S cells was prepared. tNOX was also found to be resistant to heating at 50° C. for 10 min. Heating to 50° C. for 10 min and digestion with proteinase K, when combined in series, resulted in no loss of enzymatic activity and a 10-fold enrichment in enzyme specific activity from the pH 5 extracts (Table 8). Heating at 80° C. for 10 min resulted in a complete loss of NADH oxidase activity from the pH 5 extracts. Between 37° C. and 50° C. there was no loss of soluble activity as the result of the 10 min heat treatment.

The heat inactivation of the capsaicin-inhibited NADH oxidase demonstrated two forms of the activity in the pH 5 extracts. One form (ca 25%) was inhibited by capsaicin and resistant to heating. The other (ca. 75%) was not inhibited by capsaicin and was more susceptible to heat inactivation.

Protease resistance, including resistance to proteinase K, was demonstrated in several different ways. In control experiments, a standard protease assay based upon increase in $A_{280}$ absorbing material in the supernatant after 10% trichloroacetic acid precipitation in the cold for 10 min and centrifugation was used. Hemoglobin, albumin and casein were efficiently cleaved by proteinase K (0.5 μg/ml) at 37° C. with a near optimum pH of about 8. The capsaicin-inhibited NADH oxidase activity was resistant to protease inactivation under these same conditions. Besides proteinase K, tNOX was also resistant to digestion by trypsin, chymotrypsin, subtilisin, thermolysin, pepsin, lysylamino peptidase C, and V-8 protease. Slight (<20%) activation of the NADH oxidase activities sometimes were observed, but none of the protease treatments resulted in a loss of activity. Hydrolysis conditions were varied from 0.002 to 20 μg/ml of protease and from 10 min to several hours or overnight.

NADH oxidase activity was recovered quantitatively after proteinase K digestion (Table 8). With prolonged proteinase K digestion there were sometimes indication of a reduction in the degree of capsaicin inhibition but total activity remained unchanged.

Following proteinase K digestion, FPLC was used to obtain a fraction enriched in capsaicin-inhibited NADH oxidase in greater than 95% yield and 10-fold increase in specific activity (Table 8) in the molecular weight range of 50 to 180 kD. The activity did not correlate with total protein but was displaced to lower molecular weights with an average of about 70 kD. This activity was inhibited by capsaicin. When resolved on SDS-PAGE, the material from the FPLC exhibiting maximum NADH oxidase activity correlated most closely with a 34 kD component. Also present in the active fractions were lesser amounts of proteins at 22, 17 and <10 kD.

Purification was monitored by analytical SDS-PAGE. The pH 5 extract contained a distinct subset of proteins compared to the starting HeLa S cells. The complexity of the mixture was reduced greatly by heating to 50° C. A number of contaminating proteins were present in the denatured protein of the pellet and absent from the soluble proteins of the supernatant following heating. Bulk protein was reduced further by treatment with proteinase K. With the exception of major bands at 34 kD and 36 kD, none of the proteins remaining after the proteinase K digestion were at molecular weights of <10 kD. Following FPLC, the 34 kD band was concentrated in fractions to the right of the main high molecular weight peak whereas the 36 kD band was most concentrated in fractions to the left of the main high molecular weight protein peak. Final purification resolution of the 34 and 36 kD bands was achieved by preparative SDS-PAGE.

Fractions to the left of the main protein peak of the FPLC fractions that were enriched in the 36 kD band and fractions to the right of the main protein peak that contained the capsaicin-inhibited NADH oxidase activity and a mixture of 34 and 36 kD species, were utilized for preparative SDS-PAGE to purify both the 34 and 36 kD proteins to homogeneity. When the fractions from the preparative SDS-PAGE were incubated in the presence of NADH, serum albumin and reduced glutathione for 10 min followed by the addition of dilute hydrogen peroxide, enzymatic activity was reconstituted. The reconstituted enzymatic activity correlated only with those fractions containing the 34 kD band.

Also purified to homogeneity by preparative SDS-PAGE were the 17 and 22 kD components. These proteins lacked significant NADH oxidase activity under conditions where the activity was reconstituted in those fractions containing the 34 kD component.

Compared to HeLa S plasma membranes, the reconstituted activity after SDS-PAGE was enriched 500-fold and 2.5-fold compared to the native FPLC fraction 25 exhibiting the greatest enrichment in the 34 kD protein. The yield of 34 kD material was 1–2 mg protein/10 ml packed cells (from 10 L of cultured HeLa S cells, density $0.6 \times 10^6$ cells/ml).

The 36 kD material, which was ultimately identified as glyceraldehyde-3-phosphate dehydrogenase, exhibited a mass by MALDI mass spectroscopy of 35.9 kD.

Fractions with NADH oxidase activity inhibited by capsaicin when purified or partially purified from the pH 5 extracts of HeLa S cells exhibited anomalous behavior on SDS-PAGE. Protein bands interacting with antisera prepared using 34 (33.5) kD tNOX from culture media conditioned by growth of HeLa S cells at molecular weights in multiples of 34 kD were observed. Material that at one point separated at 34 kD by preparative SDS-PAGE subsequently appeared at molecular weights of 68 or 136, demonstrating the formation of multimers stable on SDS-PAGE. These multimers were found under either reducing or non-reducing conditions. Boiling and increasing or decreasing the amount of DTT were without consistent effect. 50 mM NaCl tended to reduce multimerization. However, if the salt was removed by dialysis or ultrafiltration, the activity and identifiable bands frequently disappeared from solution. This was attributed to extensive multimerization, with the formation of amyloid rods.

When incubated in the presence of substrate, concentrated solutions enriched in the capsaicin-inhibited NADH oxidase tended to lose activity rapidly. Activity could not be restored by adding additional NADH. Generally the loss was faster when the NADH concentration was increased. The loss of activity was accompanied by the formation of microcrystals in the solution. When examined by electron microscopy, the preparations first appeared amorphous. However, when suspended in uranyl acetate or phosphotungstic acid, the preparations were seen to contain 10 nm wide amyloid rods of varying length with a discernable pattern of subunits. These amyloid rods were insoluble in all solvents tested to date (base, acid, glycerol, ethanol, organics, trifluoroacetic acid).

The 34 kD tNOX was resistant to trypsin, pepsin and all other proteases examined (V-8, lysylamino peptidase C, cathepsin D, chymotrypsin, subtilisin and thermolysin). Protease treatment failed to affect NADH oxidase activity inhibited by capsaicin or to hydrolyze the 36 kD band cut from gels, cut from ProBlott PVDF membranes following transfer or in solution (i.e. after elution from preparative SDS-PAGE). Despite repeated attempts under conditions where other proteins, e.g. albumin, were readily cleaved, the 34 kD band never yielded peptides in response to protease treatment.

The 34 kD protein associated with capsaicin-inhibited NADH oxidase activity appeared to have characteristics of an extremely hydrophobic protein surface as evidenced by its tendency to multimerize to form amyloid rods and to form multimeric species on SOS-PAGE that separated at molecular weights in apparent multiples of 34 kD.

Despite the apparent presence of methionines (Table 9), the 34 kD tNOX, when multimerized as amyloid rods, was resistant to cyanogen bromide both before or after alkylation with vinylpyridine. Hydrolysis with 0.03 M HCl, 0.25 N oxalic acid or 0.25 M acetic acid, each tried individually for 8 h at 100° C. as described [Smith and Zhou (1990) *Meth. Enzymol.* 193, 374–389], also failed to yield analyzable peptides. Denaturing conditions (pH 11, urea, ammonium carbonate, SDS, heating, guanidinium thiocyanate) failed to promote protease cleavage of the protein or automated sequencing.

The amino acid composition of each of the different protein bands eluting with the peak of capsaicin-inhibited NADH oxidase activity of the FPLC material was determined from fractions resolved on preparative SDS-PAGE, and transferred to Problott PVDF paper.

The 36 kD band which lacked NADH oxidase activity yielded an amino acid composition fitting most closely that of glyceraldehyde-3-phosphate dehydrogenase. The 36 kD material also exhibited glyceraldehyde-3-phosphate dehydrogenase activity and yielded 25 residues of N-terminal sequence identical with that of glyceraldehyde-3-phosphate dehydrogenase.

The 34 kD peptide was distinct from both the 36 kD material and from the other peptides present (Table 9). The composition was enriched in hydrophobic amino acids (ca. 63%). There were approximately 3 methionines per 34 kD monomer. Cystine was present in the 34 kD peptide but was absent from the 17 kD peptide. While the 34 and the lower molecular weight peptides were similar in amino acid composition, they were not identical. Especially pronounced were differences in what are usually among the most reliably analyzed amino acids, leucine, phenylalanine, lysine and glycine. The content of basic amino acids (13%) as well as the proportion of Asp+Asn and Glu+Gln (21%) was similar for each of the five proteins (Table 9). The amino acid composition of the 34 kD species exhibited relatedness but not identity to a small number of dehydrogenases and oxidases, none of which appeared to be identical to the capsaicin-inhibited NADH oxidase.

The 22 kD peptide was distinct from the 17, 34 and 36 kD components and represented yet another protein potentially related to dehydrogenases or oxidases. The 22 kD fraction was without NADH oxidase activity when analyzed as an apparently homogeneous protein.

Rabbit sera were prepared against a 33.5 kD component of culture medium conditioned by the growth of HeLa cells that exhibited an antitumor sulfonylurea-[Morré et al. (1995) Biochim. Biophys. Acta 1240:11–17] and capsaicin-inhibited [Morré et al. (1995) Proc. Natl. Acad. Sci. USA 92:1831–1835] NADH oxidase activity and was capable of binding [$^3$H]-LY181984. These antisera cross-reacted on Western blots with the 34 kD and with the 68 kD and 136 multimeric bands of the material from the FPLC separations enriched in capsaicin-inhibited NADH oxidase activity. No reactivity was observed with preimmune sera.

Antibodies specific for the plasma membrane tNOX and the shed forms in urine and serum of cancer patients and animals with neoplastic disorders are useful, for example, as probes for screening DNA expression libraries or for detecting or diagnosing a neoplastic disorder in a sample from a human or animal. The antibodies (or second antibodies which are specific for the antibody which recognizes tNOX) can be bound to a substance which provides a cofactor, inhibitor, fluorescent agent, chemiluminescent agent, magnetic particle or other detectable signal. Suitable labels include but are not limited to radionuclides, enzymes, substrates, magnetic particles and the like. United States patents describing the use of such labels include, but are not limited to, U.S. Pat. Nos. 3,817,837; 3,850,752; 3,939,350; 3,996,345; 4,277,437; 4,275,149; 4,331,647; 4,348,376; 4,361,544; 5,444,744; 4,460,561; 4,624,846; 4,366,241; 5,716,595; among others. For use in therapeutic regimens, the antibody of the present invention can be coupled to a therapeutic radionuclide, a chemotherapeutic agent, a ribonucleolytic agent or a toxin. See, among others, U.S. Pat. Nos. 5,541,297, 6,395,276.

The monoclonal antibodies and corresponding hybridoma cell lines of this invention are useful for prevention, detection, diagnosis, and treatment of neoplastic cells, neoplastic tissue, and cancer in humans, animals, and in culture. The monoclonal antibodies and hybridoma cell lines of this invention are useful for generating anti-idiotypic tNOX antibodies that are useful as cancer vaccines. The monoclonal antibodies and hybridoma cell lines of this invention inhibit, slow the growth of, and kill cancer cells.

The monoclonal antibodies of the present invention can be incorporated into therapeutic compositions for the treatment of a neoplastic condition in a human or animal, where that neoplastic condition is characterized by the expression of the tNOX protein on the surface of the neoplastic cells. The monoclonal antibody can be used as is, or it can be conjugated with an antineoplastic agent such as a therapeutic radionuclide including but not limited to, $^{131}$I, $^{125}$I, $^{99}$Te, $^{188}$Re, $^{111}$In, $^{90}$Y, $^{211}$At, $^{77}$Br, $^{177}$Lu, 211, among others, or a therapeutic drug such as an anthracycline, daunomycin, doxorubicin, cis-platin, among others.

The monoclonal antibodies of the present invention can be conjugated to a detectable agent using methods well known to the art, for example to a radionuclide for use in imaging methods done with the patient or animal suspected of a neoplastic condition. Such radionuclides include $^{131}$I, $^{125}$I, $^{123}$I, $^{99}$Te, $^{211}$At, $^{188}$Re, $^{111}$In, $^{90}$Y, $^{177}$Lu. For diagnostic imaging, the preferred radiohalogens include $^{123}$I and $^{131}$I, and for positron tomographic imaging $^{18}$F, $^{75}$Br and $^{76}$Br are desirable. Preferred radiohalogens for in vitro radioimmunoassays include $^{131}$I and $^{125}$I. Conjugation and imaging techniques are well known to the art. Alternatively, the monoclonal antibodies of the present invention can be incorporated into enzyme linked immunoassays or into detectable reagents for use in staining slides or tissue samples or for use in kit-type assays using any of a variety of known sensitive detection formats such as dipsticks, solid phase immunoassays, among others. While prior art imaging compositions and methods designed for use with neoplasias have relied on a detectable antibody specific for a particular type of neoplasia. The antibodies of the present invention are advantageous in that they are specific for all neoplastic cells; i.e., they react with all types of cancer cells including without limitation prostate cancer cells, ovarian cancer cells, lymphoma cells, breast cancer cells, colon cancer cells and brain cancer cells.

The monoclonal antibodies of the present invention can be administered to patient to prevent metastasis in patient with a neoplastic condition, for example, after a procedure which might have disrupted the integrity of a tumor. The monoclonal antibodies inhibit tumor cell growth. Administration of the antibodies can also prevent development of a neoplastic disorder in a patient susceptible to or suffering from a neoplastic disorder. The antineoplastic activity of the monoclonal antibodies of the present invention can be improved by conjugation with a therapeutic radionuclide or an chemotherapeutic agent.

A therapeutic composition typically contains from about 0.1% to about 90% by weight of a therapeutic agent of the present invention in a pharmaceutically acceptable carrier. Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol and the like). For intravenous injections, water soluble versions of the compounds may be administered by the drip method, whereby a pharmaceutical formulation containing the antibody and a physiologically acceptable excipient is infused. Physiologically acceptable excipients may include for example, 5% dextrose, 0.9% saline, Ringer's solution or other suitable excipients as know to the art. Intramuscular formulations, e.g., sterile formulation of the antibody of the present invention can be dissolved and administered in a pharmaceutical excipient such as Water for Injection, 0.9% saline or 5% glucose solution. A suitable insoluble form of the antibody preparation of the present invention can be prepared and administered as a suspension in an aqueous medium or in a pharmaceutically acceptable oil, such as an ester of a long chain fatty acid (e.g., ethyl oleate). Immunochemotherapeutic and radioimmunotherapeutic methodologies are well known to the art.

A topical semi-solid ointment formulation typically contains a concentration of the antibody from about 1 to about 20%, in a carrier such as a pharmaceutical cream base.

Various formulations for topical use include drops, tinctures, lotions, creams, solutions and ointments containing the active ingredient and various supports and vehicles. The optimal percentage of the therapeutic antibody preparation in each pharmaceutical formulation varies according to the formulation itself and the therapeutic effect desired in the specific pathologies and correlated therapeutic regimens.

Conventional methods, known to those of ordinary skill in the art of medicine, especially oncology and radiology, can be used to administer the pharmaceutical formulation to the patient. Typically, the pharmaceutical formulation is administered to the patient in an intravenous injection, intra-tumor injection, intraperitoneal injection, intrapulmonary, intrauterine, sublingual, intrathecal or intramuscular, subcutaneous routes, among others. For a neoplastic skin condition, the antibody compositions of the present invention can be administered via a topically applied cream, ointment or the like. In addition, the pharmaceutical formulations can be administered to the patient via injectable depot routes of administration such as by using 1, 3 or 6 month depot injectable or biodegradable materials and methods.

Regardless of the route of administration, the therapeutic or imaging agent of the present invention typically is administered at a daily dosage of 0.01 mg per kg body weight. the pharmaceutical formulation can be administered in multiple doses per day if desired, to achieve the total desired daily dose.

The effectiveness of the method of treatment can be assessed by monitoring the patient for known signs or symptoms of the neoplastic disorder. Parameters for assessing treatment efficacy are well known to the art.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; Fitchen, et al. (1993) Annu. Rev. Microbiol. 47:739–764; Tolstoshev, et al. (1993) in *Genomic Research in Molecular Medicine and Virology*, Academic Press; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein. Antibody vaccines are described in Dillman R. O. (2001) *Cancer Invest.* 19(8):833–841. Durrant L. G. et al. (2001) *Int J. Cancer* 1;92(3):414–20 and Bhattacharya-Chatterjee M, (2001) *Curr. Opin. Mol. Ther.* February; 3(1):63–9 describe anti-idiotype antibodies. Many of the procedures useful for practicing the present invention, whether or not described herein in detail, are well known to those skilled in the arts of molecular biology, biochemistry, immunology, and medicine.

Monoclonal or polyclonal antibodies, preferably monoclonal, specifically reacting with the tNOX of the present invention, may be made by methods known in the art. See e.g., Harlow and Lane (1988) *Antibodies: A Laboratory Manual*, Cold Spring Harbor Laboratories; and Goding (1986) *Monoclonal Antibodies: Principles and Practice*, 2d ed., Academic Press, New York.

All references cited in the present application are incorporated by reference herein to the extent that there is no inconsistency with the present disclosure.

The following examples are provided for illustrative purposes, and are not intended to limit the scope of the invention as claimed herein. Any variations in the exemplified antibodies, epitopes, purification methods, diagnostic methods, preventative methods, treatment methods, and other methods which occur to the skilled artisan are intended to fall within the scope of the present invention.

EXAMPLES

Pooled sera. Pooled sera were collected from the patient population of the Michiana Hematology-Oncology Clinic, South Bend, Ind. and from the patient population of St. Elizabeth Hospital of Lafayette, Ind. Only cancer patients with active disease (Stage III or Stage IV) were identified at the time of collections. Sera were frozen after collection and stored frozen at −20° C. Prior to assay, samples were thawed and maintained at 4° C. between thawing and assay.

Spectrophotometric tNOX Assay. NADH oxidase activity was determined as the disappearance of NADH measured at 340 nm with 430 nm as reference using an SLM Aminco (Lake Forest, Calif.) DW-2000 spectrophotometer in the dual wavelength mode of operation or a Hitachi (Tokyo, Japan) U3210 spectrophotometer at 340 nm with continuous recording over 5 or 10 min intervals once steady-state rates were obtained. The reaction mixture contained 50 mM Tris-Mes buffer (pH 7.0), 2 mM KCN to inhibit any potential mitochondrial oxidase activity, and 150 µM NADH in a total volume of 2.5 ml. Assay was at 37° C. with constant stirring. With purified fractions, 1 µM reduced glutathione was added to reduce the protein in the presence of substrate and human serum albumin, 0.1 mg/ml, as a protein source of thiols. After 10 min, 0.03% hydrogenperoxide was added (or oxidized glutathione) to reoxidize the protein under renaturing conditions and in the presence of substrate to start the reaction. A millimolar extinction coefficient of 6.22 was used to determine NADH disappearance. To determine capsaicin inhibition, capsaicin in DMSO was added to a final concentration of 1 µM (0.1% DMSO) and the rate of NADH oxidation determined over 10 min. Capsaicin at a final concentration of 100 µM (0.2% DMSO) was then added and the assay was continued for an additional 10 min.

NADH oxidase activity can also be measured using an Hitachi (Tokyo, Japan) U3210 spectrophotometer over 5 min intervals at 37° C. The activity was determined as the disappearance of NADH measured at 340 nm. The reaction mixture included sample, 50 mM Tris-Mes, pH 7.0, 2 mM KCN and 150 µM NADH in a total volume of 2.5 ml and at 37° C. with stirring. A millimolar extinction coefficient of 6.22 was used to determine NADH disappearance.

An alternative assay procedure is the use of a dithiodipyridyl substrate as described in Morré et al. (1999) *Mol. Cell. Biochem.* 207:7–13.

Estimation of Protein. Protein concentrations were determined by the bichinchoninic acid (BCA)/copper assay

[Smith et al. (1985) *Anal. Biochem.* 100, 76–85] (Pierce Chemical Co., Rockford, Ill.) using bovine serum albumin as standard.

Isolation of a protein with capsaicin-inhibited NADH oxidase activity from pooled cancer sera. Two protocols were developed to isolate the NADH oxidase protein. Pooled sera were diluted 1:10 with 100 mM Tris-Mes, pH 8.0 buffer and applied to a 9×10 cm DEAE-cellulose column. The column was then eluted with a series of buffers of decreasing pH (8.0, 7.0, 6.0, 5.5, 5.0, 4.5, 4.0, 3.5) and assayed for capsaicin-inhibited NADH oxidase. The eluates with activity were concentrated by centricon (Amicon, now Millipore Corporation, Bedford, Mass.) to a final volume of approximately 2 ml and applied onto a 2.8×20 cm Sephadex G-200 (Pharmacia Corporation, Peapack, N.J.) gel filtration column. The proteins were eluted with 50 mM Tris-HCl, pH 7.0 at a flow rate of 0.3 ml/min. The fractions eluted from the size-exclusion column which contained capsaicin-inhibited NADH oxidase activity were pooled and concentrated. Further purification used a BioRad preparative gel electrophoresis system (BioRad Column, Model 491 Preparative Cell). The degassed 10% acrylamide resolving gel was left standing overnight to allow complete polymerization, and then a 2.9% acrylamide stacking gel overlayed thereon. The sample was diluted 1:1 with sample buffer (0.06 M Tris-HCl, pH 6.8, 2% SDS, 5% β-mercaptoethanol, 10% glycerol and 0.025% bromophenol blue), boiled for 5 min, cooled on ice and loaded onto the BioRad (Hercules, Calif.) system. Separation was at constant power of 12 W with an elution buffer flow rate of 0.5 ml/min. Fractions of 2.5 ml were collected after the blue dye front had eluted. The fractions were analyzed by sodium dodecyl sulfate-polyacrylamide gel electrophoresis (SDS-PAGE, slab gels) and assayed for NADH oxidase activity inhibited by capsaicin.

To reconstitute NADH oxidase activity after preparative SDS-PAGE, 1 µM reduced glutathione was added to reduce the proteins in the presence of substrate. Human serum albumin (0.1 mg/ml) was added, when required, as a protein source of thiols. After 10 min, 0.03% hydrogen peroxide was added (or 100 µM oxidized glutathione) to reoxidize the protein under renaturing conditions and in the presence of substrate to start the reaction.

The second protocol was as follows: A fraction from approximately 150 ml of pooled cancer sera was prepared by ammonium sulfate precipitation (30 to 50% saturation). The ammonium sulfate precipitate was resuspended in about 15 ml of 50 mM Tris-HCl, pH 7.0 and dialyzed overnight at 4° C. against distilled water. Further purification was by isoelectric focusing using a Rotofor Preparative IEF Cell (BioRad, Hercules, Calif.). To 5 ml of the resuspended ammonium sulfate precipitate were added 3% CHAPS, 15% glycerol, 5 M urea and 1.5% ampholytes at pH 3–10 (BioRad) in a final volume of 60 ml. The sample was cooled to 4° C. and focused at constant power of 12 W for 4 to 5 h. Twenty fractions were collected and assayed for pH and NADH oxidase activity. The fractions containing capsaicin-inhibited NADH oxidase activity were pooled from 3 to 5 rotofor separations, the pooled material was concentrated, and it was applied to a 2.8×20 cm Sephadex G-200 column. Finally, fractions containing the capsaicin-inhibited NADH oxidase activity from this step were pooled and concentrated. The final purification step was preparative SDS-PAGE using the BioRad Column Model 491 Preparative Cell described above.

Preparation of antisera. The material eluting as 33.5 kD material isolated from culture media conditioned by growth of HeLa cells with capsaicin-inhibited NADH oxidase activity [Wilkinson et al. (1996) *Arch. Biochem. Biophys.* 336:275–282] was further purified by preparative SDS-PAGE and stained with Coomassie Blue on 10% acrylamide gels. The band with an electrophoretic mobility corresponding to an apparent molecular weight of 33.5 kD was excised, diced and macerated in 0.5 ml Freund's Complete Adjuvant and 0.5 mL phosphate-buffered saline and further homogenized by forcing through an 18 gauge needle and then a 22 gauge needle. The mixture was used as immunogen for antisera generation in a male New Zealand white rabbit (6 months old, Hazelton HRP, Inc., Denver, Pa.). The rabbit was boosted 3 weeks later with a second gel slice corresponding to the first. The rabbit was bled at approximately 1 week intervals and serum was prepared as described [Wilkinson et al. (1996) *Arch. Biochem. Biophys.* 336:275–282].

Isolation of tNOX from HeLa Cell Surface. To HeLa S cells (whole cells) from 10 L of culture media, 6 ml of 0.1 M sodium acetate, pH 5.0 was added. The cells were obtained frozen (Cellex Biosciences, Minneapolis, Minn.). The cells were thawed at room temperature and diluted 1:1 (original cell volume minus the 6 ml of pH 5.0, 0.1 M sodium acetate) and incubated at 37° C. for 1 h to release the proteins. The cells were removed by centrifugation (17,000 rpm, 60 min, Sorvall centrifuge, 30,000×g) and the cell-free supernatants containing tNOX (fully active and drug inhibitable) were refrozen and stored in 1 ml aliquots at −70° C.

Approximately 16 ml aliquots of the above supernatant material were thawed at room temperature and heated to 50° C. for 10 min in 1 ml aliquots for uniform heating. The denatured proteins were removed by centrifugation (6,000 rpm, 5 min, Eppendorf centrifuge in 1 ml aliquots). Full activity was retained from this step.

The pH of the heat-stable supernatant was adjusted to 7.8 by addition of 0.1 M sodium hydroxide. Tritirachium album proteinase K (Calbiochem, San Diego, Calif.) was added (4 µg/ml) and incubated at 37° C. for 1 h; full enzymatic activity and drug responsiveness were maintained. The reaction was stopped either by freezing or by adding 0.1 M phenylmethylsulfonyl fluoride (PMSF) in ethanol to yield a final concentration of 10 mM PMSF. Activity was measured by oxidation of NADH (loss of absorbance at 340 nm) as described herein and inhibition of the rate of NADH oxidation by capsaicin was determined.

The proteinase K digest (12 ml) was applied to a Pharmacia (Pharmacia Corporation, Peapack, N.J.) HiLoad 26/60 FPLC Gel Filtration column. The running buffer (eluant) was 50 mM NaCl, 20 mM Tris-HCl, pH 7, and the flow rate was 1 ml/min.

Immunoblotting. Proteins were separated on 10% SDS-PAGE as described and then transferred by electroblotting onto nitrocellulose. To block unspecific antibody binding sites, the blot was placed in a solution of 5% bovine serum albumin, 10 mM Tris-HCl, 150 mM NaCl and 0.1% Tween 20 (TBS-T) for 15 min. The blocking solution and the blot were placed in the primary antibody solution (1:1000) overnight at 4° C. with shaking. The blots were washed with TBS-T four times for 15 min each after which the blots were placed into secondary antibody solution (goat anti-rabbit linked to alkaline phosphatase, Jackson Immunoresearch Laboratories, West Grove, Pa., 1:25,000 in TBS-T) for 30 min at room temperature with shaking. The blot was washed with TBS-T three times for 15 min each and placed in a mixture of 0.33/mg/ml nitro blue tetrazolium and 0.16 mg/ml of 5-bromo-1-chloro-3-indolyl phosphate prepared in 100 mM Tris, pH 9.5, containing 100 mM NaCl and 5 mM MgCl$_2$ and incubated with shaking until the purple color of positive bands appeared. The color development reaction was stopped by placing the blots in 20 mM Tris, pH 8, containing 5 mM EDTA.

Mass spectroscopy (MALDI). Mass spectra were obtained on a Voyager BioSpectrometry Workstation matrix-assisted laser desorption ionization time-of flight (MALDI-TOF) mass spectrometer (Perspective Biosystems, Framingham, Mass.). Sinapinic acid was used as the matrix at a concentration of 10 mg/ml in 70:30 0.1% trifluoroacetic acid:acetonitrile. Spectra were obtained in the positive mode with an acceleration voltage of 28,125 V and a laser attenuation of 408.

Cyanogen bromide digestion. For cyanogen bromide digestion, the proteins separated by 8% SDS-PAGE were electroblotted to ProBlott PVDF membrane according to Towbin et al. [Towbin et al. (1979) *Proc. Natl. Acad. Sci. USA* 76, 4350–4354]. SDS-PAGE were pre-electrophoresed with 0.1 mM thioglycolate to block free radicals. Regions containing proteins of interest on ProBlott PVDF membrane were cut into small pieces and placed in 10 mg/ml CNBr (dissolved in 70% formic acid) overnight in the dark at room temperature. The digested solutions were then collected and dried under nitrogen. The residues were rewetted with water and dried twice to reduce acid residues. The dried peptide fragments were resuspended in sample buffer and the pH of the samples was adjusted to neutrality with 1 M Tris. The digested fragments were separated by HPLC as described above on a discontinuous 16% acrylamide peptide gel as described by Schagger and Von Jagow [Schagger and Von Jagow (1987) *Anal. Biochem.* 166, 368–379].

Alternatively, gel slices were digested with CNBR as proteins were electro-eluted from gel slices. In addition, the CNBR digestion was carried out using alkylated material. For pyridethylation, the proteins were resuspended in 6 M urea, 0.25 M Tris, pH 8.5 and 2.5 µl β-mercaptoethanol (total volume of 100 µl). The sample was sealed under nitrogen and incubated 2 h at 37° C., after which 2.5 µl of 4-vinylpyridine was added and the mixture incubated 15 min and dried. The sample was desalted by HPLC and used for cyanogen bromide digestion as described above.

Analytical SDS-PAGE Electrophoresis. Sodium dodecyl sulfate-polyacrylamide gel electrophoresis (SDS-PAGE) was performed with the buffer system of Laemmli [Laemmli, U. K. (1990) *Nature* 227, 680–685] on acrylamide slab gels. Proteins were denatured in sample buffer by boiling for 3 min and analyzed by SDS-PAGE (12% acrylamide). The standard marker proteins were a mixture of phosphorylase b (92 kD), bovine serum albumin (66 kD), chicken egg ovalbumin (45 kD), bovine erythrocyte carbonic anhydrase (29 kD), bovine pancreas trypsinogen 24 kD), soybean trypsin inhibitor (20 kD) and "-lactalbumin from bovine milk (14.2 kD) or prestained molecular weight markers (low molecular weight range, BioRad) for protein staining or immunoblotting, respectively. The gel as stained for protein using 0.1% Coomassie Brilliant Blue R-250 or silver [Butcher and Tomkins (1985) *Anal. Biochem.* 148, 384–388].

Molecular weight determination. Subunit molecular weight was determined by SDS-polyacrylamide gel electrophoresis [Butcher and Tomkins (1985) *Anal. Biochem.* 148, 384–388] using the molecular weight protein markers described in the preceding paragraph. Native molecular weight was determined by chromatography on a Pharmacia (Pharmacia Corporation, Peapack, N.J.) FPLC Superose 12 column using thyroglobulin (669 kD), apoferritin (443 kD), P-amylase (200 kD), bovine serum albumin (66 kD), carbonic anhydrase (29 kD) and cytochrome c (12 kD) as standards.

Amino acid composition. Amino acid composition was determined using Waters (Milford, Mass.) Pico*Tag™ amino acid analysis system. Briefly, regions of blots (ProBlott PVDF membrane (Applied Biosystems, Foster City, Calif.) stained with Coomassie blue) containing proteins of interest were cut into small pieces (1 mm square) and placed into a 6×50 mm borosilicate tube. The proteins were hydrolyzed in the vapor phase with constant boiling HCl and phenol at 110° C. for 24 h. Following hydrolysis, the samples were vacuum dried and the free amino acids were derived with phenyl isothiocyanate (PITC) to yield N-PTH(phenylthiohydantoin) amino acids. These were separated by a Waters HPLC system and compared to standard amino acids (Pierce, Rockford, Ill.) which had been processed along with the samples.

Electron microscopy. Amyloid rod preparations were negatively stained on carbon-coated grids with 2% aqueous uranyl acetate. Specimens were photographed at a primary magnification of 44,000× using a Philips (FEI, Hillsboro, Oreg.) EM 200 electron microscope.

Histological staining. Reaction of MAB 12.1 with cell borders used formalin-fixed (10% neutral formalin) and paraffin-embedded HeLa cells or human carcinoma reacted with affinity purified IgG from culture media of MAB 12.1 hybridoma grown in a Cellmax system. Deparaffinized slides were hydrated, treated for 5 min with 3% hydrogen peroxide and carried through an antigen retrieval protocol (0.01 M citrate buffer at pH 6.0 and microwaved at 700 W for 5 minutes). Tissue sections were then covered with normal goat serum followed by MAB diluted to achieve a final antibody concentration of about 0.2 µg/µl, or Tris buffer as a control. Slides were incubated 1 hr at room temperature. After incubation Super Sensitive MultiLink (BioGenex, San Ramon, Calif.) was added (5 min) followed by Super Sensitive Label (BioGenex, San Ramon, Calif.). Visualization was with alkaline phosphatase-conjugated streptavidin and New Fuchsin substrate (BioGenex, San Ramon, Calif.). For cytological reaction, it was necessary then to restore cell surface NADH oxidase activity by contacting with 1 µM reduced glutathione for 10 min followed by 0.03% hydrogen peroxide or 100 µM oxidized glutathione for 10 min, both in the presence of 150 µM NADH.

Immunoprecipitation. 2.5 ml sera samples were solubilized with 2% NP-40 and precleared. To preclear, 50 µl of 72 mg/ml of protein-A-Sepharose were added and incubated at 4° C. for 4 hr with shaking. The protein A-Sepharose was removed by centrifugation. To immunoprecipitate the tNOX mouse ascites, 2.5 µl containing 5 µg antibody, were added and incubated overnight at 4° C. with shaking. For crude polyclonal post-immunization sera, 2.5 µl, 180 µg total protein, were added. Next, protein-A-Sepharose was added, collected by centrifugation, and serially washed twice with 0.1% NP-40, once with PBS and once with water. The pellets were boiled in SDS sample buffer and the proteins were separated on 12% SDS-PAGE and immunoblotted as described above.

Growth of Cells. Attached cells were grown and treated in 35×10 mm plastic dishes in 2.5 ml culture medium as described (Morré et al. (1995) *Proc. Natl. Acad. Sci. USA* 92:1831–1835). Growth was determined from cell numbers estimated by counting the number of cells over areas defined by a grid of 1 mm squares after 24, 48, and 72 h of treatment.

After 96 h of treatment, cells were trypsinized with 0.05% Sigma 1× trypsin (Sigma-Aldrich, St. Louis, Mo.) containing 0.53 mM EDTA for 1 min and the released cells were counted using a hemocytometer.

For determinations of apoptosis, cells were fixed in methanol followed by the addition of fluorescent dye DAPI (4',6-diamidino-2-phenylindole) (Morré et al. (1995) *Proc. Natl. Acad. Sci. USA* 92:1831–1835). Working antibody dilutions were determined by titration with inhibition of tNOX activity for cancer patient sera or inhibition of HeLa cell growth as the end points. For most purposes, a dilution of 1:1000 was utilized.

Propagation of hybridomas. Propagation of hybridomas followed standard protocols described in Schook (1987) *Monoclonal Antibody Production Techniques and Applications. Immunology Series*, Vol. 3, pp 99–101. Marcel Dekker, Inc.

Estimation of protein disulfide-thiol interchange activity. Protein disulfide-thiol interchange activity was estimated from the rate of restoration of activity by refolding of reduced and randomly oxidized (scrambled) and initially inactive ribonuclease A. Ribonuclease A activity was measured using a spectrophotometric assay based on hydrolysis of cCMP as the RNase substrate [Lyles and Gilbert (1991) *Biochemistry* 30:613–619]. Scrambled RNase (0.036 mg) was incubated together with 0.45 mM cCMP in 50 mM Tris-Mes buffer, pH 6.5, at 30° C. in a final volume of 3 ml. In the absence of membranes, the scrambled RNase was inactive (2% of the native RNase). In the presence of membranes, the scrambled RNase became active as evidence from an increase in $A_{296}$ from the RNase catalyzed hydrolysis of cCMP. cCMP was added to a final concentration of 0.45 mM to initiate the reaction. The increase of the absorbance at 296 nm was recorded over 25 min and the concentrations of cCMP were determined ($\in = 0.19$ mM$^{-1}$ cm$^{-1}$). Measurements were with a Hitachi U3210 spectrophotometer with a thermostatic cell compartment maintained at 30° C. with continuous stirring.

Preparation of scrambled RNase substrate. To prepare the oxidized, denatured RNase substrate (scrambled RNase), native RNase A (Sigma, Type 1-AS from bovine pancreas) (30 mg/ml) was incubated 1 h at 35° C. in 50 mM Tris-acetate, pH 8.6, containing 9 M urea and 130 mM DTT [Hilson et al. (1984) *Meth Enzymol.* 107:281–291].

The fully reduced protein was isolated by adjusting the pH to 5.0 with glacial acetic acid, the solution was applied to a gel filtration column (Sephadex G-25, Pharmacia, Parsippany, N.J.), and the RNase was eluted from the column with degassed 0.1 M acetic acid and used directly or further processed to produce scrambled RNase. Protein concentration was estimated from spectrophotometric measurement at 280 nm using native RNase A as standard. For preparation of scrambled RNase, the reduced RNase was diluted to about 0.5 mg/ml with 0.1 M acetic acid. Solid urea then was added to a final concentration of 10 M after which 0.1 M sarcosine hydrochloride was added and the pH adjusted to 8.5 with 1 M Tris. The mixture then was incubated in the dark for 2–3 days during which time the protein was randomly oxidized. The scrambled product was recovered by acidification to pH 4 with glacial acetic acid and size exclusion chromatography over Sephadex G-25 in 0.1 M acetic acid.

TABLE 1

Effect of MAB 12.1 (1:1000) on NOX activity of sera

| Sera | MAB | No addition | +1 μM Cap | + μM Cap |
|---|---|---|---|---|
| Cancer | − | 1.6 ± 0.2 | 1.0 ± 0.13 | 1.0 ± 0.17 |
|  | + | 1.0 ± 0.16 | 1.0 ± 0.17 | 1.0 ± 0.15 |
| Normal | − | 0.7 ± 0.13 | 0.7 ± 0.14 | 0.7 ± 0.16 |
|  | + | 0.7 ± 0.15 | 0.7 ± 0.13 | 0.7 ± 0.14 |

Mean ± standard deviation from 5 determinations.
Sera were pooled patient sera.

TABLE 2

Immunoprecipitation of tNOX with MAB 12.1
nmoles/min/100 μl serum

|  | No addition | 1 μM capsaicin | 100 μM capsaicin |
|---|---|---|---|
| Preimmune | 0.85 ± 0.04 | 0.6 ± 0.4 | 0.5 |
| MAB 12.1 | 0.55 ± 0.07 | 0.6 ± 0.04 | 0.5 ± 0.08 |

Supernatant activity assayed

TABLE 3

Response of mouse myeloma SP-2 cell growth to MAB 12.1 after 72 h

|  | Dilution | Cells × 10$^4$/ml |
|---|---|---|
| Control |  | 144 |
| MAB 12.1 | 1:100 | 109 |
|  | 1:1000 | 119 |
| MAB 12.5 | 1:100 | 104 |

Initial inoculum = 4 × 10$^4$ cells/ml

TABLE 4

Antibody inhibition of tNOX of cancer sera is anticompetitive or uncompetitive

| #1 Ascites | | | |
|---|---|---|---|
| 5 μl | Ab (1:10) in PBS | $i = \frac{1.85 - 1.75}{1.85}$ | = 0.054 |
| 10 μl | Ab (1:10) | $i = \frac{1.85 - 1.5}{1.85}$ | = 0.189 |
| 15 μl | Ab (1:10) | $i = \frac{1.85 - 1.3}{1.85}$ | = 0.297 |
| 20 μl | Ab (1:10) | $i = \frac{1.85 - 0.9}{1.85}$ | = 0.51 |
| 25 μl | Ab (1:10) | $i = \frac{1.85 - 0.9}{1.85}$ | = 0.51 |

$i = \frac{vo - vi}{vo}$ vo: unihibited initial reaction
vi: inhibited initial reaction

TABLE 5

Response of tTIP sera of cancer patients to MAB 12.1.
Assay with DTNB substrate.

| Sera | MAB 12.1 | Km | $V_{max}$ | Capsaicin inhibition |
|---|---|---|---|---|
| Breast CA | − | 1.25 mM | 1.7 nmoles/min/100 μl | −0.6 |
|  | + | 10 mM | 1.7 nmoles/min/100 μl | −0.2 |

TABLE 6

Effect of MAB 12.1 on Growth of Mammary Cells in Culture

| Cell line | MAB 12.1 | Cells/mm² after 72 h |
|---|---|---|
| MCF 10A mammary adenoma | None | 45 |
|  | 1:1000 | 41 |
| BT-20 mammary adenocarcinoma | None | 110 |
|  | 1:1000 | 69 |

TABLE 7

Depletion of NADH oxidase activity inhibited by capsaicin from plasma membranes by incubation of HeLa S cells at 37° C. for 2 h in the presence of 0.1 M sodium acetate, pH 5.0, to effect the release of tNOX.
Frozen HeLa S cells were thawed at room temperature, incubated and plasma membranes were then isolated from the incubated cells and analyzed for NADH oxidase activity inhibited by capsaicin.

| Treatment | NADH oxidase activity, nmoles/min/mg plasma membrane protein | | |
|---|---|---|---|
|  | No capsaicin | 1 μM capsaicin | 100 μM capsaicin |
| PBS, pH 7 2 h, 37° C. | 0.8 ± 0.1 | 0.2 ± 0.02 | 0.2 ± 0.02 |
| 0.1 M sodium acetate, pH 5 2 h, 37° C. | 0.26 ± 0.1 | 0.2 ± 0.01 | 0.15 ± 0.02 |

Average of two determinations ± mean average deviations.

TABLE 8

Purification of capsaicin-inhibited surface NADH oxidase activity from HeLa S cells.

| Fraction | nmoles/min/mg protein |
|---|---|
| HeLa plasma membrane | 0.8 |
| pH 5/50° C./proteinase K | 16 |
| FPLC fraction 25 | 160 |
| Preparative SDS-PAGE | 400 |

TABLE 9

Amino acid composition comparing the 36, 34, 22, 17 and 9.5 kD peptides from a preparative SDS-PAGE of tNOX-enriched FPLC fractions to Problot PVDF membranes.

| Amino acid | Mole percent | | | | |
|---|---|---|---|---|---|
|  | 36 kD (N = 2) | 34 kD (n = 2) | 22 kD (n = 3) | 17 kD (n = 4) | 9.5 kD (n = 1) |
| Asp + Asn | 12.7 ± 0.2 | 10.9 ± 0.7 | 10.0 ± 2.5 | 10.4 ± 0.4 | 10.6 |
| Glu + Gln | 7.3 ± 1.3 | 10.3 ± 1.2 | 11.1 ± 1.8 | 10.4 ± 0.6 | 10.2 |
| Ser | 7.1 ± 0.3 | 8.2 ± 0.6 | 7.5 ± 1.8 | 7.6 ± 1.3 | 8.2 |
| Gly | 11.0 ± 0.8 | 9.8 ± 1.5 | 11.6 ± 1.9 | 12.0 ± 1.8 | 12.5 |
| His | 2.7 ± 0.2 | 2.2 ± 0.1 | 2.8 ± 0.2 | 2.4 ± 0.7 | 2.2 |
| Arg | 3.3 ± 0.1 | 3.9 ± 0.5 | 5.2 ± 1.1 | 4.6 ± 0.5 | 3.9 |
| Thr | 5.9 ± 0.8 | 4.8 ± 0.2 | 5.1 ± 1.9 | 5.3 ± 0.5 | 5.5 |
| Ala | 10.1 ± 0.4 | 6.7 ± 0.3 | 8.2 ± 2.1 | 7.8 ± 0.6 | 7.8 |
| Pro | 3.8 ± 0.2 | 3.7 ± 0.3 | 4.3 ± 0.8 | 4.3 ± 0.5 | 3.5 |
| Tyr | 2.5 ± 0 | 2.5 ± 0.2 | 2.7 ± 0.4 | 3.1 ± 0.6 | 3.2 |
| Val | 8.4 ± 0.4 | 8.8 ± 0.9 | 6.9 ± 0.4 | 7.4 ± 0.5 | 7.9 |
| Met | 1.1 ± 0.1 | 1.1 ± 0.4 | 0.85 ± 0.15 | 0.6 ± 0.3 | 0.6 |
| Cys2 | 0.4 ± 0.1 | 0.7 ± 0.5 | 0.6 ± 1.07 | — | 0.6 |
| Ile | 5.5 ± 0.3 | 5.9 ± 0.4 | 5.0 ± 0.7 | 5.2 ± 0.4 | 5.0 |
| Leu | 6.4 ± 0.1 | 10.5 ± 1.0 | 8.1 ± 1.0 | 7.7 ± 0.1 | 8.9 |
| Phe | 4.1 ± 0.2 | 2.5 ± 0.1 | 3.1 ± 0.1 | 4.2 ± 0.1 | 3.3 |
| Lys | 6.9 ± 0.4 | 7.7 ± 0.8 | 6.0 ± 0.5 | 6.6 ± 0.7 | 6.2 |

Results are averages of independent determinations ± standard or mean average deviations.

We claim:

1. A monoclonal antibody, specific for a disulfide-thiol interchange/NADH oxidese protein of a cell surface protein (tNOX), wherein said tNOX occurs in serum, in urine and on surfaces of neoplastic cells of a human or animal with a neoplastic disorder and does not occur in serum, urine and cell surfaces of a human or animal without a neoplastic disorder, and wherein said monoclonal antibody is produced by hybridoma line 12.1, American Type Culture collection Accession No. PTA-4206.

* * * * *

UNITED STATES PATENT AND TRADEMARK OFFICE
CERTIFICATE OF CORRECTION

PATENT NO. : 7,053,188 B2 Page 1 of 1
APPLICATION NO. : 10/373579
DATED : May 30, 2006
INVENTOR(S) : D. James Morré et al.

It is certified that error appears in the above-identified patent and that said Letters Patent is hereby corrected as shown below:

In Column 3, at both line 52 and line 53:

"(5 mm.)" should be replaced with --(5 min.)--

Signed and Sealed this

Tenth Day of April, 2007

JON W. DUDAS
*Director of the United States Patent and Trademark Office*